United States Patent
Glass et al.

(10) Patent No.: US 6,586,256 B1
(45) Date of Patent: Jul. 1, 2003

(54) CHEMICAL SENSORS AND METHOD OF USE

(75) Inventors: Timothy E. Glass, State College, PA (US); Joseph Raker, State College, PA (US); Ricardo Moran, Washington, DC (US)

(73) Assignee: The Penn State Research Foundation

( * ) Notice: Subject to any disclaimer, the term of this patent is extended or adjusted under 35 U.S.C. 154(b) by 0 days.

(21) Appl. No.: 09/562,202

(22) Filed: May 2, 2000

Related U.S. Application Data

(60) Provisional application No. 60/132,418, filed on May 4, 1999.

(51) Int. Cl.[7] ............................................. G01N 21/64
(52) U.S. Cl. ...................... 436/164; 436/172; 552/101; 564/305
(58) Field of Search ..................... 436/164, 172; 564/304; 552/101

(56) References Cited

PUBLICATIONS

Chemical Communication Journal. "Dual–mode electro-chromism switched by proton transfer: dynamic redox properties of bis (diarylmethylenium) –type dyes". Suzuki et al. 2001.*

The Journal of Organic Chemistry. "Cooperative Ratiometric Chemosensors: Pinwheel Receptors with an Integrated Fluorescence System". Raker et al. Oct. 2001.*

Journal of the American Chemical Society: "Cooperative Ratiometric Chemosensors: Pinwheel Receptors with Metal Ion Recognition Properties". Glass. Apr. 2000.*

Tetrahedron. "General synthetic methods for preparation of pinwheel receptors". Raker et al. Nov. 2001.*

Journal of the American Chemical Society. "Molecular "compassess" and "gyroscopes." III. Dynamics of a Phenylene Rotor and Clathrated Benzene in a Slipping Gear Crystal Latice". Dominguez et al. Jun. 2002.* de Silva et al., "Signaling Recognition Events with Fluroscent Sensors and Switches," Chem. Rev., 97: 1515, 1997.

Schmidtchen, F., "Synthesis of an Abiotic Ditopic Receptor Molecule," Tetrahedron Letters, 25: 4361, 1984.

de Silva et al., "Fluroescent signalling of the brain neurotransmitter γ–aminobutyric acid and related amino acid zwitterions," Chem. Commun., 2191, 1996.

Wieland, H. and H. Kloss, "Uber einige neue Abkommlinge des Triphenylmethans," Annalen der Chemie., 470: 201, 1929.

(List continued on next page.)

*Primary Examiner*—Jill Warden
*Assistant Examiner*—Latoya Cross
(74) *Attorney, Agent, or Firm*—Akerman Senterfitt; Stanley A. Kim

(57) ABSTRACT

Chemical sensor compositions and methods for quantifying analytes are described. The chemical sensors include analyte-binding moieties and reporter moieties covalently attached to a framework including two trityl groups connected by a linear spacer such as ethyne or butadiyne. The sensors chelate an analyte across the acetylene axis of the molecule to stabilize the molecule in an eclipsed rotamer conformation. This conformation causes the sensors to emit a measurable signal. Also disclosed are methods of making the chemical sensors, methods of using the chemical sensors, and kits for quantifying analytes using the chemical

18 Claims, 21 Drawing Sheets

RM=REPORTER MOIETY
B =ANALYTE-BINDING MOIETY

Energy Minimized Structure of 2 (Macromodel™)

OTHER PUBLICATIONS

Hart et al., "Molecular Design for Hosts in Crystalline Host–Guest Complexes," J. Am. Chem. Soc., 106: 4043, 1984.

Kelly et al., "A Molecular Brake," J. Am. Chem. Soc., 116: 3657, 1994.

Bouas–Laurent et al., "Cation–Directed Photochemistry of an Anthraceno–Crown Ether," J. Am. Chem. Soc., 108: 315, 1986.

Takeuchi et al., "A Strong Positive Allosteric Effect in the Molecular Recognition of Dicarboxylic Acids by a Cerium(iv) Bis[tetrakis(4–pyridyl)–prophyrinate] Double Decker," Angew. Chem. Int. Ed., 37: 2096, 1998.

Gromov et al., "A Novel Optical Sensor for Metal Ions Based on Ground–State Intermolecular Charge–Transfer Complexation," Organic Letters, 1: 1697, 1999.

Marquis, D. and J. Desvergne, "A cooperative effect in sodium cation complexation by a macrocyclic bis (9,10) anthraceno–crown ether in the ground state and in the excited state," Chemical Physics Letters, 230: 131, 1994.

Xia et al., "A Highly Selective Fluorescent Chemosensor for K+ from a Bis–15–Crown–5 Derivative," J. Am. Chem. Soc., 121: 5599, 1999.

Marquis et al., "Photoresponsive Supramolecular Systems: Synthesis and Photophysical and Photochemical Study of Bis–(9,10–anthracenediyl) coronands $AAO_nO_n$," J. Org. Chem., 60: 7984, 1995.

Ikeda et al., "Allosteric Silver(I) Ion Binding with Peripheral π Clefts of a Ce(IV) Double Decker Porphyrin," Organic Letters, 0: A, 2000.

Czarnik, A., "Desperately seeking sensors," Chemistry & Biology, 2: 423, 1995.

Sugasaki et al., "The First Example of Positive Allosterism in an Aqueous Saccharide–Binding System Designed on a Ce(IV) Bis(Porphyrinate) Double Decker Scaffold," Autopagination 2, 16: 2, 2000.

Fages et al., "Synthesis, Structural, Spectroscopic, and Alkali–Metal Cations Complexation Studies of a Bis–Anthracenediyl Macrotricyclic Ditopic Receptor," J. Org. Chem., 59: 5264, 1994.

* cited by examiner

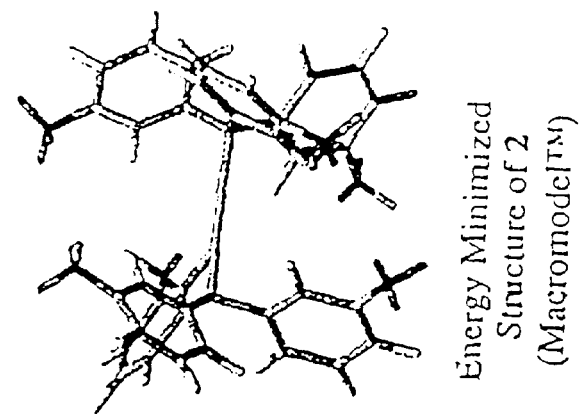
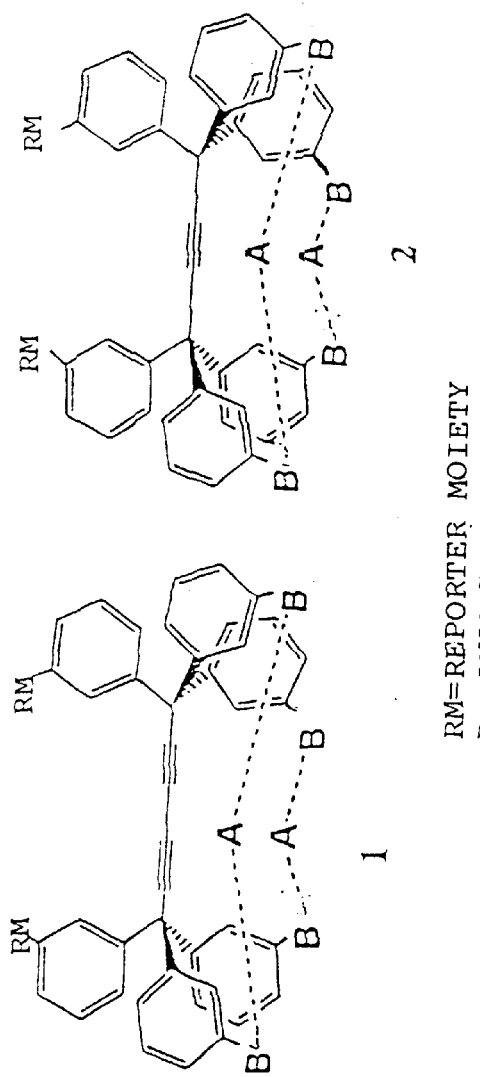
RM = REPORTER MOIETY
B = ANALYTE-BINDING MOIETY
Figure 1

Looking at compound 1 "end-on".

FIGURE 9: THE EFFECT OF INCREASING CONCENTRATIONS OF PHTHALIC ACID DIPOTASSIUM SALT ON THE FLUORESCENCE AT 363 nm OF COMPOUND 14.

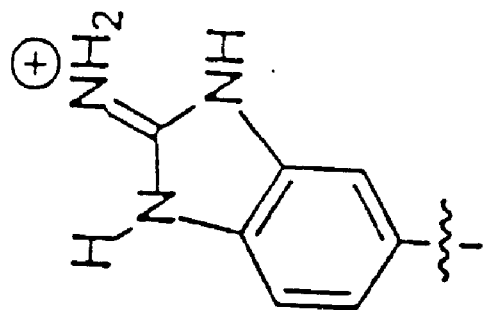
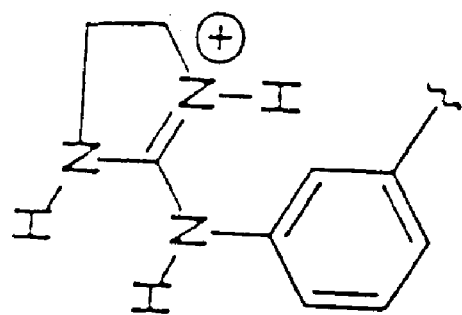
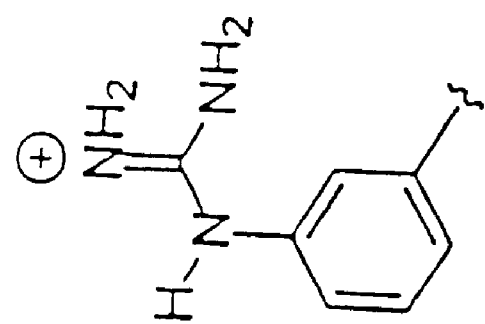
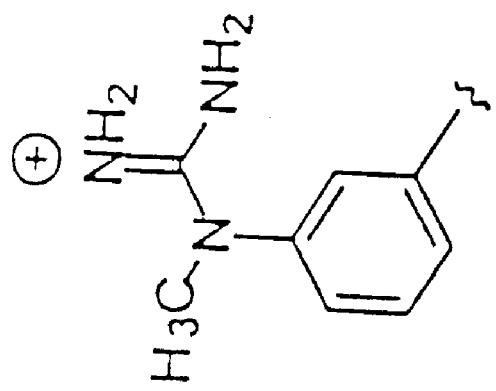
Figure 11

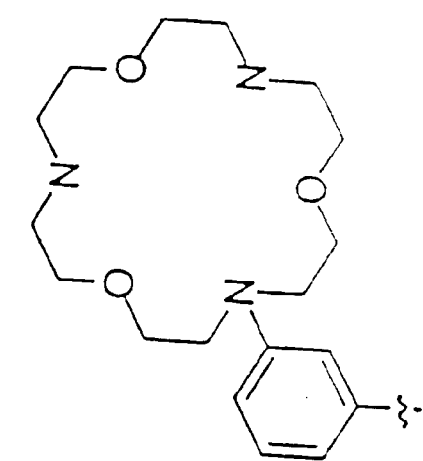
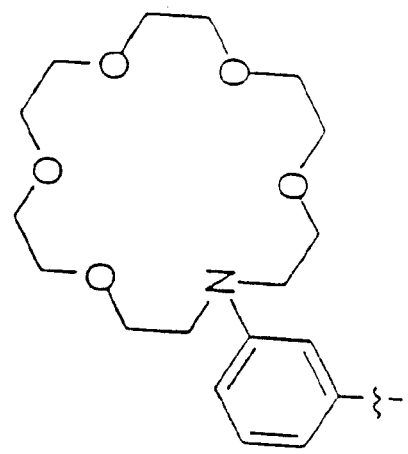
Figure 12
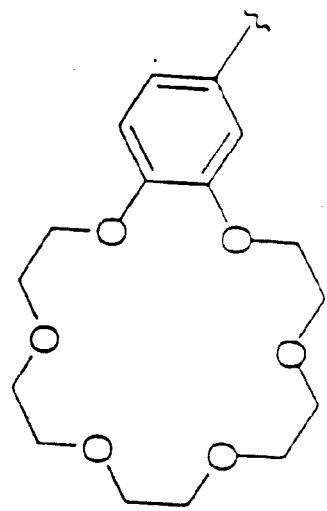

CHEMICAL SENSORS AND METHOD OF USE

CROSS REFERENCE TO RELATED APPLICATIONS

The present application claims the benefit of U.S. provisional patent application Ser. No. 60/132,418 filed May 4, 1999, which is incorporated herein by reference.

STATEMENT AS TO FEDERALLY-SPONSORED RESEARCH

This invention was made with government support under grant R1 GM59245 awarded by the National Institutes of Health. The government may have certain rights in the invention.

FIELD OF THE INVENTION

The present invention relates to compounds for quantifying analytes. In particular, the present invention relates to small molecule compounds that have analyte-binding moieties functionally linked to reporter moieties. The reporter moieties of these molecules emit a measurable signal when the analyte-binding moieties interact with the analyte.

BACKGROUND OF THE INVENTION

Chemical sensors or chemosensors are small synthetic molecules that produce a measurable signal upon interaction with a specific analyte. They are used to determine the concentration of an analyte without involving complicated analytical techniques or having to "disturb" the system being analyzed. Numerous uses for chemosensors exist. For example, in the biochemical community, they have been used as sensitive, nondestructive probes for quantifying the amount of a particular analyte in living cells. In the medical industry, chemosensors are used for quickly quantifying the amount of certain analytes in bodily fluids such as blood or urine. Myriad other applications for chemosensors exist, including, for example, monitoring pollutants in waste water and quantifying contaminants in chemical compositions. See, *Chemosensors of Ion and Molecule Recognition*, Desvergne, J- P.; Czarnik, A. W., Eds.; NATO ASI Series C: 492; Kluwer: New York, 1997; "Signaling Recognition Events with Fluorescent Sensors and Switches" de Silva, A. P.; Gunaratne, H. Q. N.; Gunnlaugsson T.; Huxley, A. J. M.; McCoy, C. P.; Radermacher, J. T.; Rice, T. E. *Chem. Rev.* 1997, 97, 1515; "Desperately Seeking Sensors" Czamik, A. W., *Chem. and Bio.* 1995, 2, 423; *Fluorescent Chemosensors for Ion and Molecule Recognition*, Czarnik, A. W. (Ed.), ACS Symp. Set. 538; ACS: Washington D.C., 1993.

Several molecules that can serve as chemosensors have previously been developed (see, e.g., http://www.molecularprobes.com). These compounds are typically designed to have an analyte-binding moiety functionally connected to a fluorescent reporter moiety. Binding of the analyte of interest by the analyte-binding moiety causes a conformational change in the chemosensor molecule that results in the modulation of the fluorescence of the reporter moiety. For example, fluorescence resonance energy transfer (FRET) may result when two fluorescent moieties are brought into close proximity by the steric change of a chemosensor molecule caused by analyte-binding. FRET alters the fluorescence emission of the reporter moiety, resulting in a measurable signal from which the analyte concentration can be extrapolated. Other chemosensor molecules produce a visible color change upon binding an analyte. Analyte-binding by these molecules alters their conformation so that in solution they absorb visible light differently and thereby cause a color change.

Three examples of chemical sensors are shown below.

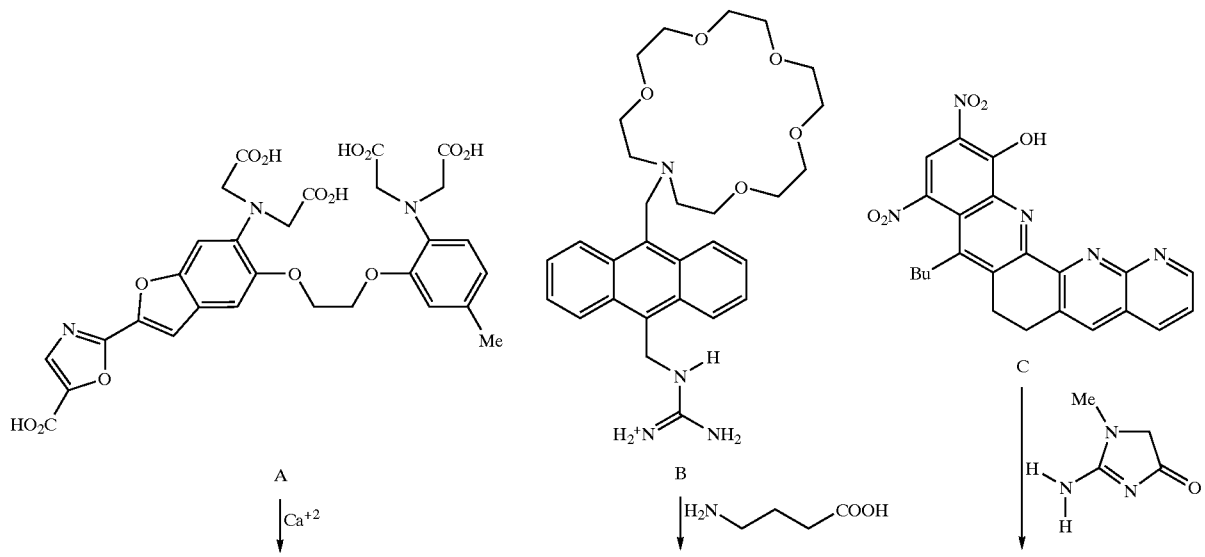

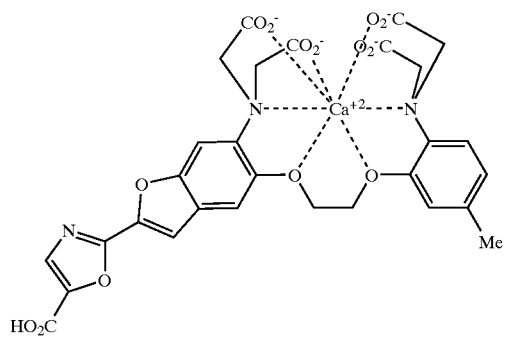

-continued

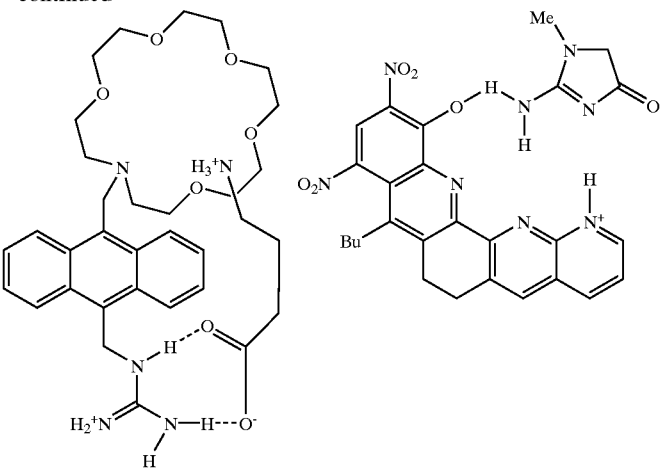

Compound A acts as a calcium sensor by exhibiting increased fluorescence intensity upon binding free $Ca^{2+}$. "Desperately Seeking Sensors" Czarnik, A. W., *Chem. and Bio.* 1995, 2, 423. Compound B is a fluorescent sensor for γ-amino butyrate, which functions in aqueous methanol. "Fluorescent Signaling of the Brain Neurotransmitter γ-Aminobutyric Acid and Related Amino Acid Zwitterions." de Silva, A. P.; Gunaratne, H. Q. N.; McVeigh, C.; Maguire, G. E. M.; Maxwell, P. R. S.; O'Hanlon. E. *Chem. Commun.* 1996, 2191. See also: "Synthesis of an Abiotic Ditopic Receptor Molecule." Schmidtchen, F. P. *Tetrahedron Lett.* 1984, 25, 4361. Compound C is a selective sensor that changes color upon binding creatinine.

Each particular chemosensor has various advantages and drawbacks that make it suitable for some applications and inappropriate for others. Many compounds are not particularly selective and/or sensitive in analyte-binding. For example, if one prepares a calcium ion sensor that also produces a signal in the presence of magnesium ions, it is not a useful sensor in systems that contain high concentrations of magnesium ions. As another example, because Compound B is a photoinduced electron transfer (PET)-based sensor, it can be activated by molecules aside from aminobutyric acid, including anything that sequesters the lone pair of the crown ether nitrogen (e.g., simple protonation).

Although the need for sensors which recognize small molecule targets is great, few have reached the state of practical utility. A common drawback of many existing chemosensors is that their molecular framework does not allow them to be easily adapted for use with different analytes or reporter readout devices. Thus, chemosensors having a molecular framework to which different moieties can be easily attached would be advantageous. For example, molecules such as, Compound D, bistrityl acetylene ("Uber einige neue Abkommlinge des Triphenylmethans." Wieland, H.; Kloss, H. Justus Liebigs Ann. Chem. 1929, 4 70, 202–21) or, Compound E, bistrityl butadiyne ("Molecular Design for Hosts in Crystalline Host-Guest Complexes." Hart, H.; Lin, L.-T. W.; Ward, D. L. *J. Am. Chem. Soc.* 1984,106, 4043–4045) would be useful for preparing frameworks for chemosensor molecules.

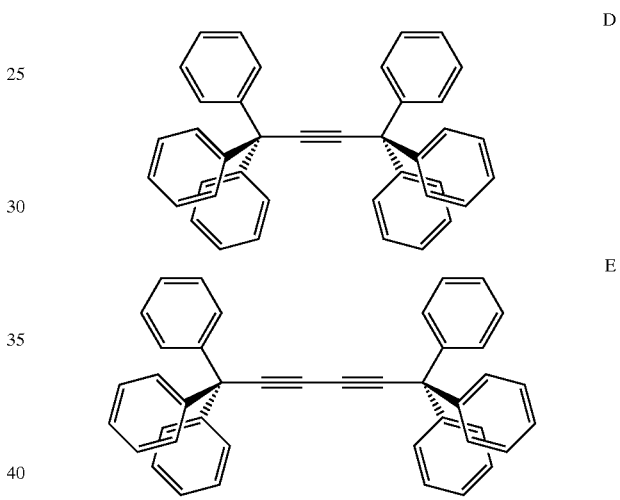

SUMMARY OF THE INVENTION

The invention relates to chemical sensors having analyte-binding moieties and reporter moieties covalently attached to a framework composed of two trityl groups connected by a linear spacer such as an ethyne or butadiyne. Each of the three phenyls of the trityl group is substituted at the meta position, two with analyte-binding moieties and one with a reporter moiety. In some cases, one or more of the phenyl groups of each trityl group are also substituted with another chemical group such as a methoxy group. The architecture of the framework allows pre-selected analyte-binding moieties and reporter moieties to be bonded to the framework by simple chemical reactions to form chemosensors useful for quantifying predetermined analytes using predetermined reporter measuring devices. Thus, chemosensors with predetermined characteristics can be readily fashioned by simply reacting appropriate analyte-binding and reporter molecules with the framework.

Each sensor molecule is capable of binding two analyte molecules by chelation of each analyte molecule between each pair of analyte-binding moieties across the linear spacer (e.g., the acetylene axis). An important feature of the invention is that in the absence of analyte, the trityl groups of the sensor molecule rotate freely about the linear spacer.

In the presence of analyte, the analyte-binding moieties engage the analyte, thereby stabilizing the molecule in an eclipsed rotamer conformation. This conformation also causes the reporter moieties to be in an eclipsed geometry, a geometry which causes the reporter moieties to signal (e.g., for fluorescent reporters, the signal is modulated fluorescence intensity or a shift in the fluorescence spectrum such as that caused by excimer fluorescence).

Chemosensor molecules within the invention feature two pairs of analyte-binding moieties that can cooperatively bind an analyte. This cooperative recognition enhances the overall affinity of the sensor for the analyte as the first analyte-binding event preorganizes the chemosensor molecule for the second analyte-binding event. Moreover, this double analyte-binding moiety design enhances the selectivity of these the chemosensors of the invention compared to those sensors having other designs.

Accordingly, the present invention features compounds having the structure:

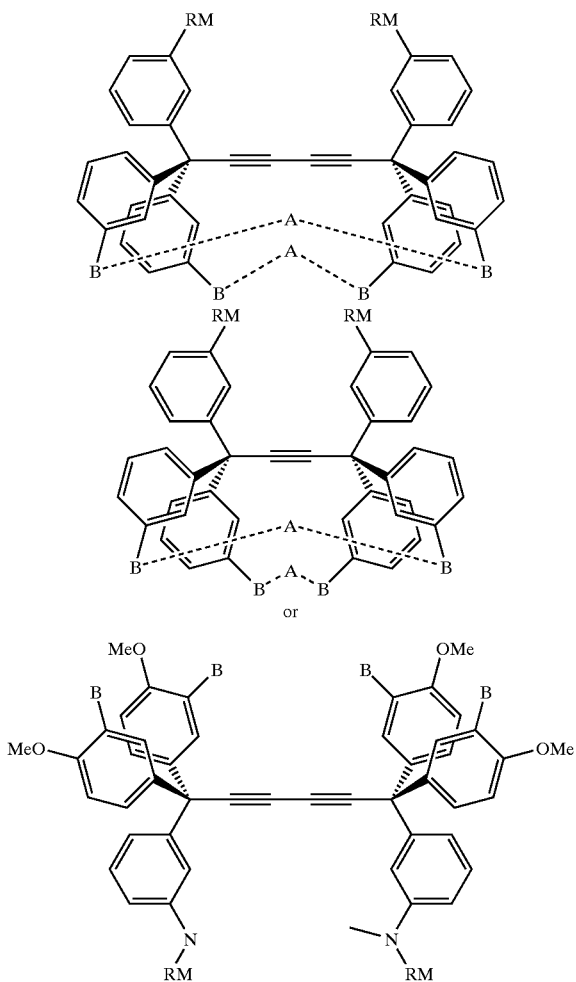

wherein B is an analyte-binding moiety and RM is a reporter moiety. A is the analyte shown interacting with the compounds. In various such compounds, B is a chemical group selected from ethylene diamine, trimethyl ethylenediamine, guanidinium, and the chemical groups shown in FIGS. 11–15. In some of these compounds, RM is a chemical group selected from napthyl, pyrenyl acetyl, and the chemical groups shown in FIG. 10. In a preferred aspect of the invention, B is ethylene diamine and RM is napthyl. In another preferred aspect of the invention, B is guanidinium and RM is napthyl. In yet another preferred aspect of the invention, B is trimethyl ethylenediamine and RM is pyrenyl acetyl. Also within the invention is Compound 8, Compound 14, and Compound 23.

The invention also includes a method of preparing a compound of the invention by covalently attaching an analyte-binding moiety and a reporter moiety to a framework molecule including bistrityl acetylene or bistrityl butadiyne.

Also featured within the invention is a method of detecting an analyte using a compound within the invention. This method includes the steps of obtaining a mixture containing an analyte; adding the compound to the mixture; and measuring a signal from the compound of the mixture. In addition, the invention includes a method of determining the concentration of an analyte using a compound of the invention. This method includes the steps of obtaining a mixture containing the analyte; adding the compound to the mixture; and quantifying a signal from the compound in the mixture.

Additionally within the invention is a kit for determining the concentration of an analyte using a compound of the invention. This kit includes the compound of the invention and instructions for using the compound to determine the concentration of the analyte. Compositions including compounds of the invention are also featured.

As used herein, the term "quantifying" means assigning a numerical value to.

By the phrase "fluorescence analyzer" is meant any machine or device that can analyze the fluorescence emitted by a sample. Examples of fluorescence analyzers include fluorimeters and flow cytometers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 shows the molecular framework and attached analyte-binding moieties and reporter moieties of two embodiments (Compound 1 and Compound 2) of the invention and the energy minimized structure of one embodiment of the invention.

FIG. 11 is a list of chemical groups useful as for binding carboxylates, phosphates, or sulfates.

FIG. 12 is a list of chemical groups useful for binding cations such as ammoniums.

DETAILED DESCRIPTION

The present invention relates to chemosensor molecules of modular design that can be triggered by analyte molecules to generate a measurable signal. In the preferred embodiments, the chemosensors have analyte-binding moieties and reporter moieties covalently attached to a framework composed of two trityl groups connected by a linear spacer, such as an ethyne or butadiyne. Each of the three phenyls of the trityl group is substituted at the meta position, two with analyte-binding moieties and one with a reporter moiety.

Framework

The framework of sensors within the invention include two base groups (e.g., trityl groups) connected by a linear spacer (e.g., ethyne, butadiyne, or similar linear molecules). Each of the two base groups serve as a structure to which a plurality of predetermined chemical groups including an analyte-binding moiety and a reporter moiety can be covalently attached. The sensor binds analytes by chelation between analyte-binding moieties across the axis formed by the linear spacer.

The base groups can be any suitable chemical group that can be covalently joined via a linear spacer and substituted with other chemical groups (e.g., those used as analyte-binding moieties or reporter moieties). Those skilled in the art can select an appropriate base group according to the particular application the chemosensor will be used for. Preferred base groups are those chemical groups having phenyl groups. A particularly preferred base group is a trityl group.

The linear spacer can be any suitable linear molecule. One skilled in the art can select the linear spacer according to the particular application the chemosensor is to used for. For example, for larger analytes, a longer linear spacer may be chosen to accommodate the size of the analyte molecule. Likewise, for smaller analytes, a shorter linear spacer may be chosen. In preferred embodiments, the linear spacer is ethyne or butadiyne.

The structure of the framework permits the base groups freely rotate about the axis formed by the linear spacer in the absence of analyte. See, e.g., "A Molecular Brake." Kelly, T. R.; Bowyer, M. C.; Bhaskar. K. V.; Bebbington, D.; Garcia, A.; Lang, F.; Kim, M. H.; Jette, M. P. *J. Am. Chem. Soc.* 1994, 116, 3657. Binding of an analyte stabilizes the sensor molecule in the eclipsed rotamer conformation (see FIG. 2 for one example). This conformation results in the loss of base group rotational freedom, thus causing an alignment of the reporter moieties in an eclipsed geometry. Such alignment causes a measurable signal to be emitted (constitutively or induced by external excitation, e.g., from an excitatory energy source) from the sensor molecule.

Figure 2:
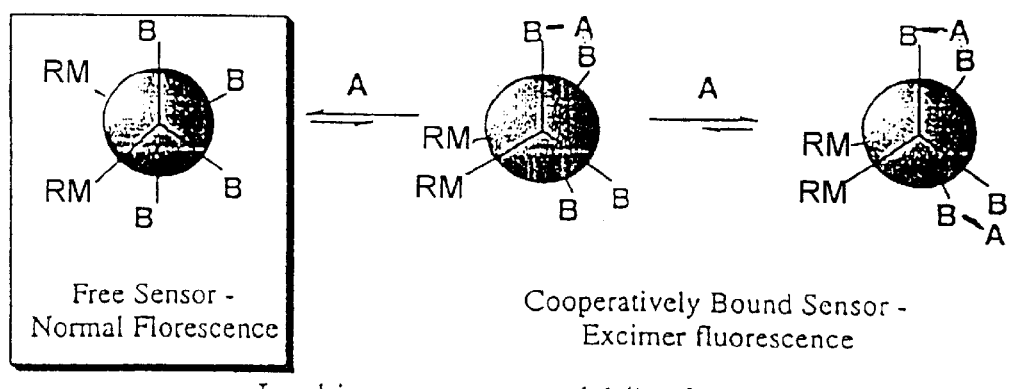
FIG. 2 shows an "end-on" view of Compound 1 where the receptor moieties are fluorophores in the presence and absence of bound analyte.

Referring to FIGS. 1 and 2, preferred chemosensors of the invention feature a framework composed of two trityl groups connected by a linear spacer (e.g., ethyne, butadiyne or the like). The three phenyl groups of each trityl group are substituted at the meta position, two with analyte-binding moieties and one with a reporter moiety. In various preferred embodiments, the analyte-binding moieties are ethylene diamine groups or guanidinium groups and the reporter moieties are napthyl groups (e.g., Compounds 8 and 14). In a particularly preferred embodiment, two of the phenyl groups that form each trityl group are also substituted with a methoxy group, the analyte-binding moieties are trimethyl ethylenediamine, and the reporter moieties are pyrenyl acetyl, groups.

Analyte-binding Moieties

The chemosensors of the invention include a plurality of analyte-binding moieties attached to the base groups. In some embodiments, the analyte-binding moieties attached to the base groups of a particular chemosensor molecule are the same. However, in other embodiments the analyte-binding moieties are different. For example, the analyte-binding moieties on one individual base group are the same but different from the analyte-binding moieties on the other base group of the chemosensor molecule. In another example, the analyte-binding moieties on one base group are different from each other. Although different analyte-binding moieties generally bind different analytes, in some cases the analyte-binding moieties are specific for the same analyte but bind different portions of the analyte.

Analyte-binding moieties useful in the invention include any chemical group that can be incorporated into a chemosensor (e.g., by covalent bonding to a base group) of the invention and react with an analyte to be quantified. Several analyte-binding moieties that can be incorporated into the sensors of the invention are known in the art. One preferred analyte-binding moiety is the ethylene diamine group. This particular group is useful for chelating divalent cations such as $Zn^{++}$, $Ca^{++}$, or $Mg^{++}$. Another preferred analyte-binding moiety is guanidinium which is useful for binding acids such as carboxylic acid. Yet another preferred analyte-binding moiety is trimethyl ethylenediamine which is useful for binding various metal ions including, for example, Ag(I), Zn(II), Hg(I), Hg(II), Fe(I), Fe(II), Co(II), Cu(I), Cu(II), Ni(II), and Cd(II). Many other analyte-binding moieties useful in the chemosensor molecules of the invention are known.

For example, the chemical groups listed in FIG. 11 are useful for binding anions such as carboxylates, phosphates, or sulfates. The chemical groups shown in FIG. 12 are useful for binding cations such as ammoniums. Used in combinations of two, these groups can bind diamines, diacids, amino acids and similar analytes which possess a combination of anionic and cationic sites.

Figure 13:
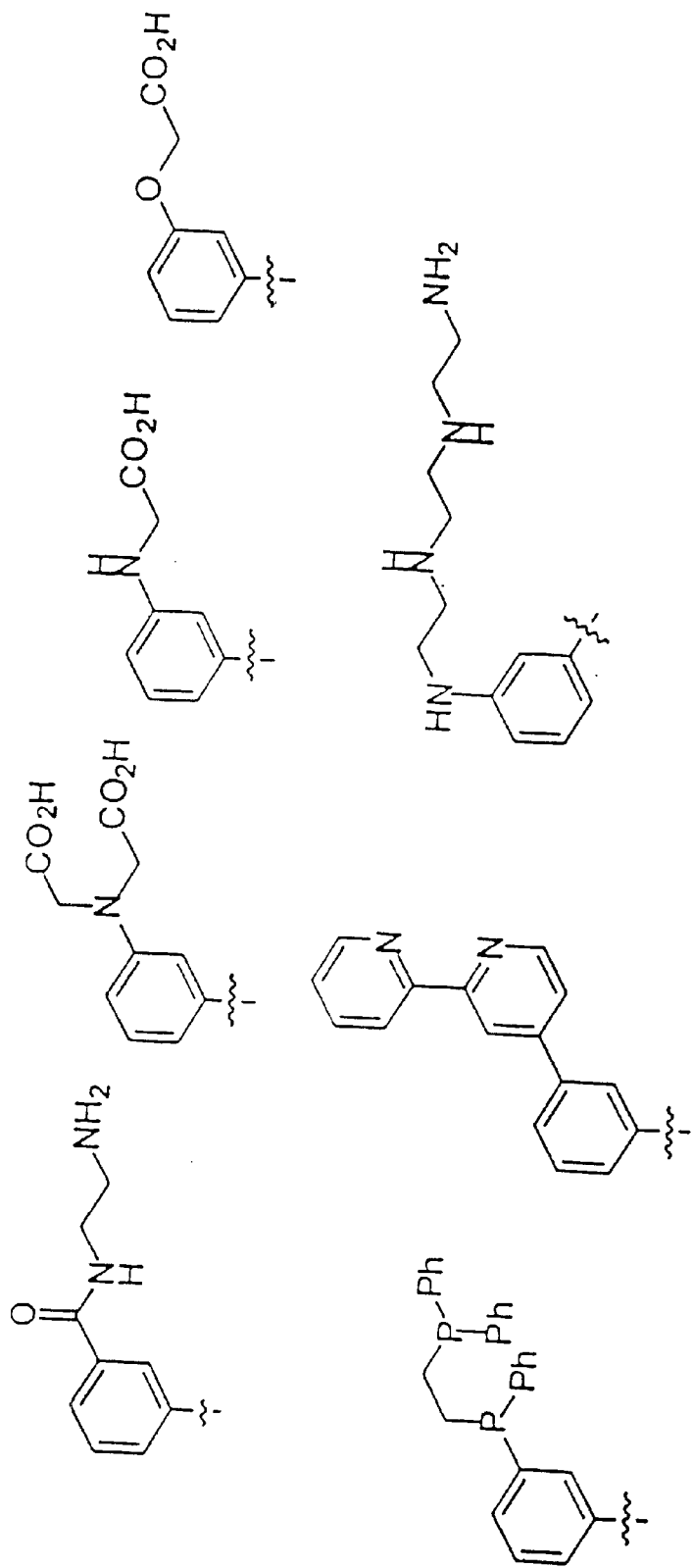
FIG. 13 is a list of chemical groups useful for binding metals such as $Ca^{++}$, $Zn^{++}$, $Mg^{++}$, $Ni^{++}$, $Pd^{++}$, $Ag^{++}$, $Au^{++}$, $Cu^{++}$, and $Mn^{++}$.
Figure 14:
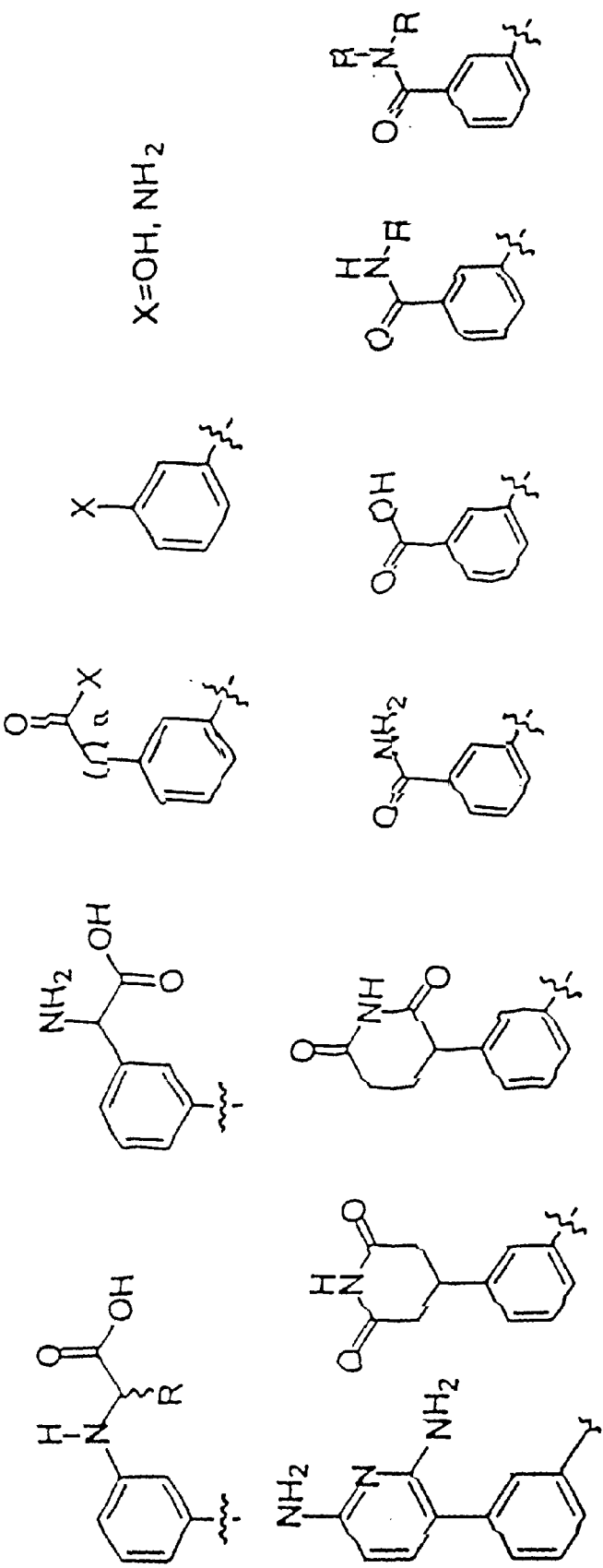
FIG. 14 is a list of hydrogen bond binding groups.

Chemical groups useful for binding metals such as $Ca^{++}$, $Zn^{++}$, $Mg^{++}$, $Ni^{++}$, $Pd^{++}$, $Ag^{++}$, $Au^{++}$, $Cu^{++}$, and $Mn^{++}$ include those listed in FIG. 13. General hydrogen bond binding groups are listed in FIG. 14. Used in combinations of two, these groups are useful for binding nucleic acids as well as peptides and amino acids.

Figure 15:
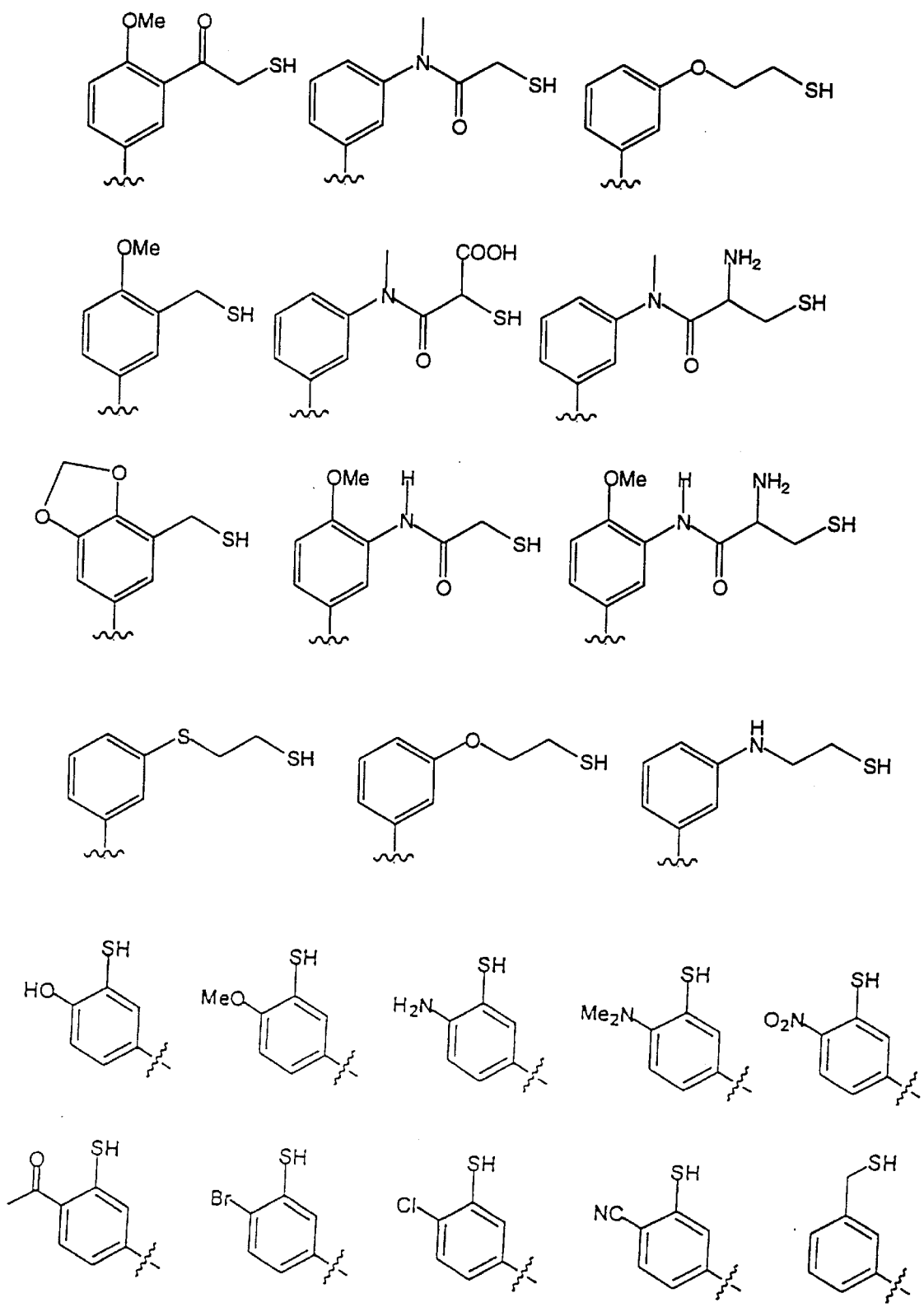
FIG. 15 is a list of thiol-binding groups.

Thiol-containing binding groups such as those shown in FIG. 15 can be used as analyte-binding groups to measure reduction potentials by observing the ratio of oxidized sensor to reduced sensor in a reaction mixture. By varying substituents on such thiol-containing compounds a range of reduction potentials can be measured.

Reporter Moieties

The chemosensors of the invention include a plurality of reporter moieties attached to the base groups. As with the analyte-binding moieties, the reporter moieties on each base group can be the same or different. Although preferred chemosensors generally incorporate two identical reporter moieties, other chemosensors within the invention utilize pairs of different reporter moieties. Depending on the particular application (e.g., readout device), such combination of different reporters may be particularly useful.

In the preferred embodiment, the identical reporters cause a signal when forced into an eclipsed geometry. In the embodiments having different reporter moieties, a measurable signal also results when the chemosensor molecule is forced into an eclipsed geometry (e.g., the proximity of two fluorescent reporters causes a measurable signal such as a FRET-induced change in emission spectrum).

Reporter moieties useful in the invention include any chemical group that can be incorporated into a chemosensor of the invention and generate a measurable signal when the sensor binds an appropriate analyte. Several reporter moieties that can be incorporated into the sensors of the invention are known in the art. Those that cause a measurable signal (e.g., modulation of fluorescence, phosphorescence, luminescence, visible color, etc.) when an analyte forces the chemosensor molecule into an eclipsed conformation are most useful. Common examples of reporter moieties are fluorophores and visible dyes. Fluorophore molecules are particularly useful in the invention because they typically cooperate to generate a measurable signal such as a change in the intensity or wavelength of fluorescence emission when placed in close proximity to each other.

Figure 10:
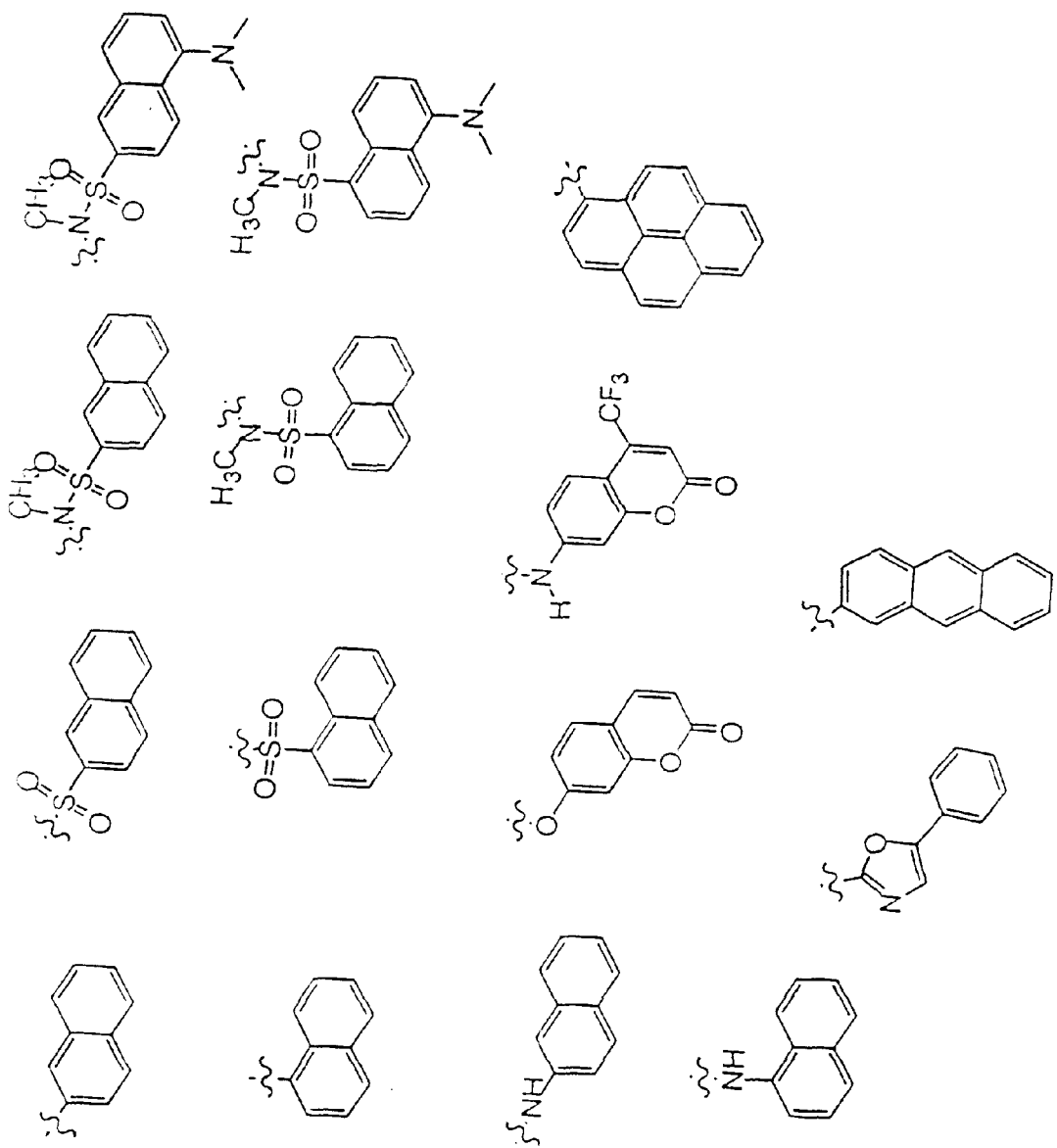
FIG. 10 is a list of fluorophores useful as reporter moieties.

Preferred reporter moieties include pyrenyl acetyl and napthyl groups. Other exemplary fluorophores useful as reporter moieties include those shown in FIG. 10.

Methods of Synthesizing Chemosensors

Various chemosensor molecules can be prepared by reacting the above-described analyte-binding moieties and reporter moieties with a molecule having a framework made up of two base groups connected by a linear spacer (e.g., bistrityl acetylene or bistrityl butadiyne). Many methods of conducting such reactions are known in the art. Preferred methods of preparing chemosensors of the invention are described below in Examples 1, 3, 5, and 6.

Methods of Use

The chemosensors of the invention can be used to determine the presence and/or concentration of an analyte in a mixture (e.g., a solution) containing one or more other chemicals. Typically, a small amount of the chemosensor is added to the mixture and the mixture is analyzed for a signal emitted by the chemosensor molecule via its reporter moieties. Among other methods known in the art, the signal can be measured for a chromophoric response by, e.g., visualizing a color change with the naked eye, measuring changes in the optical properties of mixture containing the chemical sensor (e.g., via spectrophotometry), or measuring a change in fluorescence emission intensity or an emission wavelength shift. Generally, the intensity of a given signal can be correlated with the concentration of an analyte in a mixture. By extrapolating this data, the analyte concentration can be determined quite accurately (e.g., by comparison to signal intensity observed in samples containing known concentrations of analyte). Preferred techniques for this are described below in Examples 2, 4, and 6.

Chemosensor Kits

The chemosensor compounds of the invention can be included along with one or more other components to form a kit that is useful for determining the presence and/or concentration of analyte. For example, the compounds of the invention can be packaged along with instructions for using the compounds in particular applications.

EXAMPLES

Example 1

Synthesis of Bistritylbisacetylene

Figure 3:
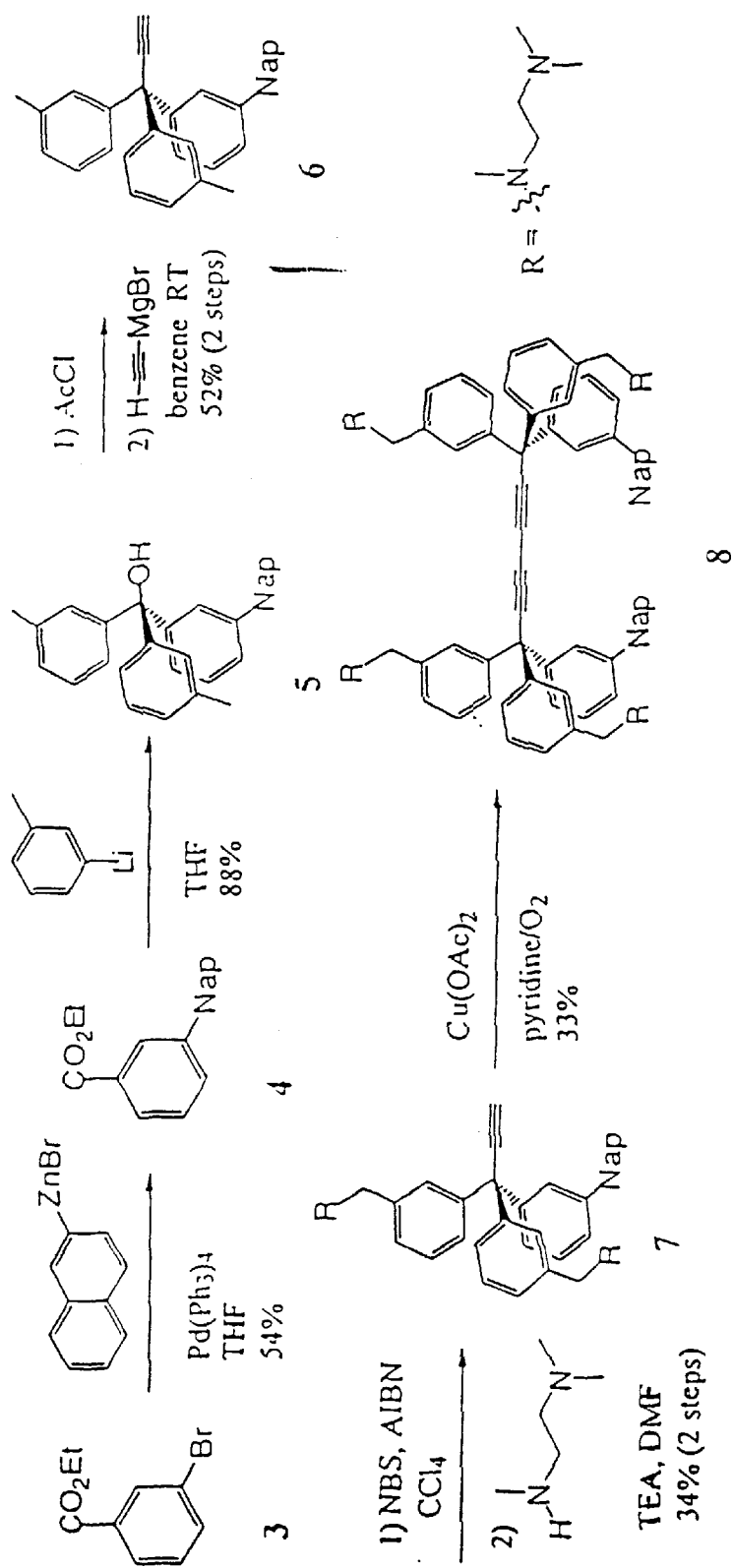
FIG. 3 shows the synthesis of Bistritylbisacetylene (Compound 8) with napthyl groups as the reporter moieties and ethylene diamine groups as the analyte-binding moieties.

Bistritylbisacetylene was synthesized according to steps A–E described below and shown in FIG. 3.

A. Synthesis of ethyl-3-(2-naphthyl)-benzoate (Compound 4): To a stirred solution of THF (250 ml) and 2-bromonaphthalene (5.06 g, 24.4 mmol), at −78° C., was added n-BuLi (10.26 ml, 25.6 mmol, 2.5M in hexanes). The reaction mixture was allowed to stir for 30 min, followed by addition of $ZnCl_2$ (26.9 ml, 26.9 mmol, 1.0 M in ether). The reaction mixture was allowed to warm to room temperature, followed by addition of $Pd(PPh_3)_4$ (2.82 g, 2.44 mmol), and ethyl-3-bromobenzoate (Compound 3) (3.71 ml, 23.19 mmol). The reaction mixture was allowed to stir at 50° C. for 12 hrs. The reaction mixture was washed with saturated $NH_4Cl$, and the aqueous layer was extracted with $CH_2Cl_2$. The organic layer was dried over $MgSO_4$, and the solvent removed in vacuo. Flash chromatography (EtOAc/Hex, 1:99) afforded Compound 4 (3.35 g, 12.12 mmol, 54%) as white crystals (mp 101–103° C.). $^1H$ NMR d 1.44 (t, J=7.1 Hz, 3H), 4.44 (q, J=7.2 Hz, 2H), 7.49–7.60 (m, 3H), 7.77 (dd, J=1.9, 8.6 Hz, 1H), 7.86–7.97 (m, 4H), 8.06 (dt, J=1.4, 7.7 Hz, 2H), 8.09 (d, J=1.0 Hz, 1H), 8.41 (t, J=1.8 Hz, 1H). $^{13}C$ NMR d 14.8, 61.5, 125.7, 126.4, 126.6, 126.9, 128.1, 128.7, 128.8, 128.9, 129.0, 129.3, 131.5, 132.1, 133.2, 134.0, 137.9, 141.7, 167.0. MS m/z 276.115 ($M^+$).

B. Synthesis of bis(3-tolyl)-3-(2-naphthyl)phenyl methanol (Compound 5): To a stirred solution of THF (175 ml) and 3-bromotoluene (2.15 ml, 17.7 mmol), at −78° C., was added n-BuLi (6.4 ml, 15.9 mmol, 2.5M in hexanes). The reaction mixture was allowed to stir for 30 minutes, followed by addition of Compound 4 (979 mg, 3.54 mmol, in 10 ml THF). The reaction mixture was allowed to warm to room temperature and then quenched with $NH_4Cl$. The aqueous layer was extracted with $CH_2Cl_2$. The organic layer was dried over $MgSO_4$, and the solvent removed in vacuo. Flash chromatography (EtOAc/Hex, 5:95) afforded Compound 5 (1.28 g, 3.08 mmol, 88%) as white crystals (mp 58–60° C.). $^1H$ NMR d 2.33 (s, 6H), 2.86 (s 1H), 7.05–7.12 (m, 4H), 7.18–7.25 (m, 5H), 7.41 (t, J=7.6 Hz, 1H), 7.46 (d, J=4.3 Hz, 1H), 7.49 (t, J=1.2 Hz, 1H), 7.62–7.70 (m, 2H), 7.75 (t, J=1.8 Hz, 1H), 7.82–7.90 (m, 3H), 7.98 (d, J=1.6 Hz, 1H). $^{13}$C NMR d 21.6, 82.1, 125.2, 125.6, 125.8, 125.9, 126.2, 126.21, 126.8, 127.1, 127.6, 127.8, 128.1, 128.14, 128.3, 128.31, 128.4, 132.5, 133.6, 137.6, 138.4, 140.6, 146.8, 147.6. MS m/z 437.1897 (M$^+$+Na).

C. Synthesis of 3,3-(bis(3-tolyl)-3-(3-(2-naphthyl) phenyl)-1-propyne (Compound 6): A solution of Compound 5 (931 mg, 2.24 mmol) and acetyl chloride (20 ml) was stirred at room temperature for 3 hours. The acetyl chloride was removed in vacuo, and the resulting solid was dried under high vacuum for 1 hour. The solid was redissolved in benzene (25 ml). To the reaction mixture was added ethynylmagnesium bromide (22.4 ml, 11.22 mmol, 0.5M in THF). The reaction mixture was stirred at room temperature for 48 hours. The reaction was quenched with NH$_4$Cl, and the aqueous layer was extracted with CH$_2$Cl$_2$. The organic layer was then dried over MgSO$_4$, and the solvent removed in vacuo. Flash chromatography (Ether/Hex, 1:99) afforded Compound 6 (489 mg, 1.16 mmol, 52%) as a viscous oil. $^1$H NMR d 2.31 (s, 6H), 2.75 (s, 1H), 7.03–7.23 (m, 9H), 7.39 (t, J=7.8 Hz, 1H), 7.44–7.49 (m, 2H), 7.59–7.68 (m, 2H), 7.84 (t, J=1.7 Hz, 1H), 7.8–7.88 (m, 3H), 8.02 (d, J=0.86 Hz, 1H). $^{13}$C NMR d 22.0, 55.9, 74.0, 90.4, 126.0, 126.2, 126.31, 126.35, 126.7, 128.0, 128.17, 128.25, 128.6, 128.70, 128.73, 128.8, 130.2, 133.0, 138.1, 138.8, 141.1, 145.1, 146.0. MS m/z 422.2035 (M$^+$).

D. Synthesis of trityl acetylene (Compound 7): A solution of Compound 6 (804 mg, 1.9 mmol), N-bromosuccinimide (712 mg, 4.0 mmol), and benzoyl peroxide (13 mg (75% solid with water), 0.308 mmol) in CCl$_4$ (20 ml) was stirred at 90° C. for 20 hours. Additional N-bromosuccinimide (178 mg, 1 mmol) was added to the solution and stirred at 90° at 20 and 29 hours, with a total reaction time of 41 hours. The reaction mixture was filtered, and the solvent removed in vacuo. Flash chromatography (2% Et$_2$O/Hexanes) afforded the impure dibromide (747 mg). To a solution of the dibromide (115 mg, 0.198 mmol) in 10% Et$_3$N in DMF (2.0 ml) was added N,N,N'-trimethyl ethylene diamine (0.50 ml, 3.96 mmol). The solution was stirred at 90° C. for 2 hours. The solvent was removed in vacuo, and Compound 7 (66 mg, 0.106 mmol, 34% yield for two steps) was isolated via flash chromatography (50% Et$_3$N/EtOAc) pure as a yellow viscous oil. $^1$H NMR d 2.15–2.18 (m, 18H), 2.36–2.43 (m, 8H), 2.74 (s, 1H), 3.49 (s, 4H), 7.11–7.14 (m, 2H), 7.18–7.27 (m, 5H), 7.34 (bs, 2H), 7.38 (t, J=7.8 Hz, 1H), 7.44–7.48 (m, 2H), 7.60–7.64 (m, 2H), 7.71 (t, J=1.7 Hz, 1H), 7.81–7.86 (m, 3H), 7.92 (bs, 1H). $^{13}$C NMR d 42.8, 46.0, 55.2, 55.9, 57.5, 63.1, 74.1, 90.2, 125.9, 126.2, 126.3, 126.4, 126.7, 128.0, 128.2, 128.3, 128.4, 128.50, 128.53, 128.6, 128.7, 128.8, 130.3, 133.0, 134.0, 138,8, 139.0, 141.1, 145.0, 145.9. MS m/z 623.4114 (M$^+$+H).

E. Synthesis of Bistritylbisacetylene (Compound 8): A solution of Compound 7 (33.0 mg, 0.053 mmol) in pyridine (distilled from CaH$_2$, oxygenated at 60° C. 15 min). To this was added Cu(OAc)$_2$ (96.0 mg, 0.530 mmol) over a period of 5 minutes. The reaction was stirred at 60° C. for 4 hours under an atmosphere of O$_2$. The reaction mixture was loaded directly on to a flash silica column, and chromatographed using 5% MeOH(H$_3$)/CHCl$_3$. Compound 8 was isolated in vacuo as a yellow viscous oil (11.0 mg, 0.0088 mmol, 33%). $^1$H NMR d 2.12–2.14 (m, 36H), 2.32–2.43 (m, 16H), 3.46 (s, 8H), 7.15–7.18 (m, 4H), 7.22–7.25 (m, 14H), 7.39 (t, J=7.7 Hz, 2H), 7.42–7.46 (m, 4H), 7.59–7.62 (m, 6H), 7.76–7.82 (m, 6H), 7.91 (bs, 2H). MS m/z 1243.7993 (M$^+$+H).

Example 2

Titration Experiments with Compound 8

Figure 4:
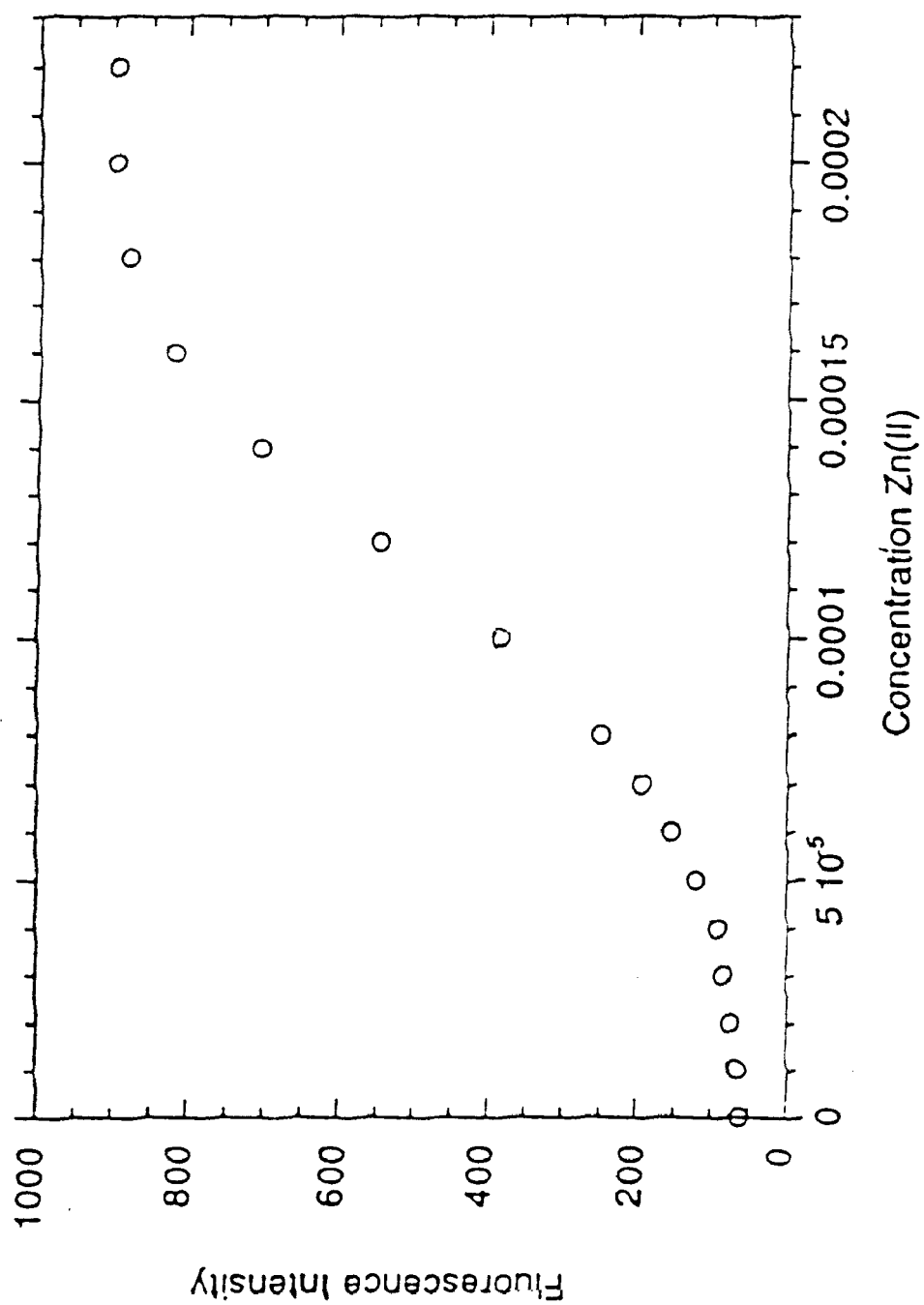
FIG. 4 is a graph depicting the titration curve of Compound 8 with zinc ions (zinc nitrate) in acetonitrile.

Referring to FIG. 4, a solution of Compound 8 in acetonitrile was made (1.0×10$^{-5}$ M). A 2 mL aliquot of this solution was placed in a quartz fluorescence cell. This solution was titrated with a solution of Zn(OAc)$_2$.6H$_2$O (1.0×10$^{-3}$ M) using 2 $\mu$l injections. Binding was followed using a Shimadzu RF-5301 PC Spectofluorophotometer with excitation at 290 nm and emission at 360 nm. The resultant data shows that Compound 8 acts as a chemosensor for zinc ions as its fluorescence increased almost 15 fold in the presence of two equivalents of zinc nitrate. The data is consistent with a 2:1 cooperative binding.

Example 3

Figure 5:
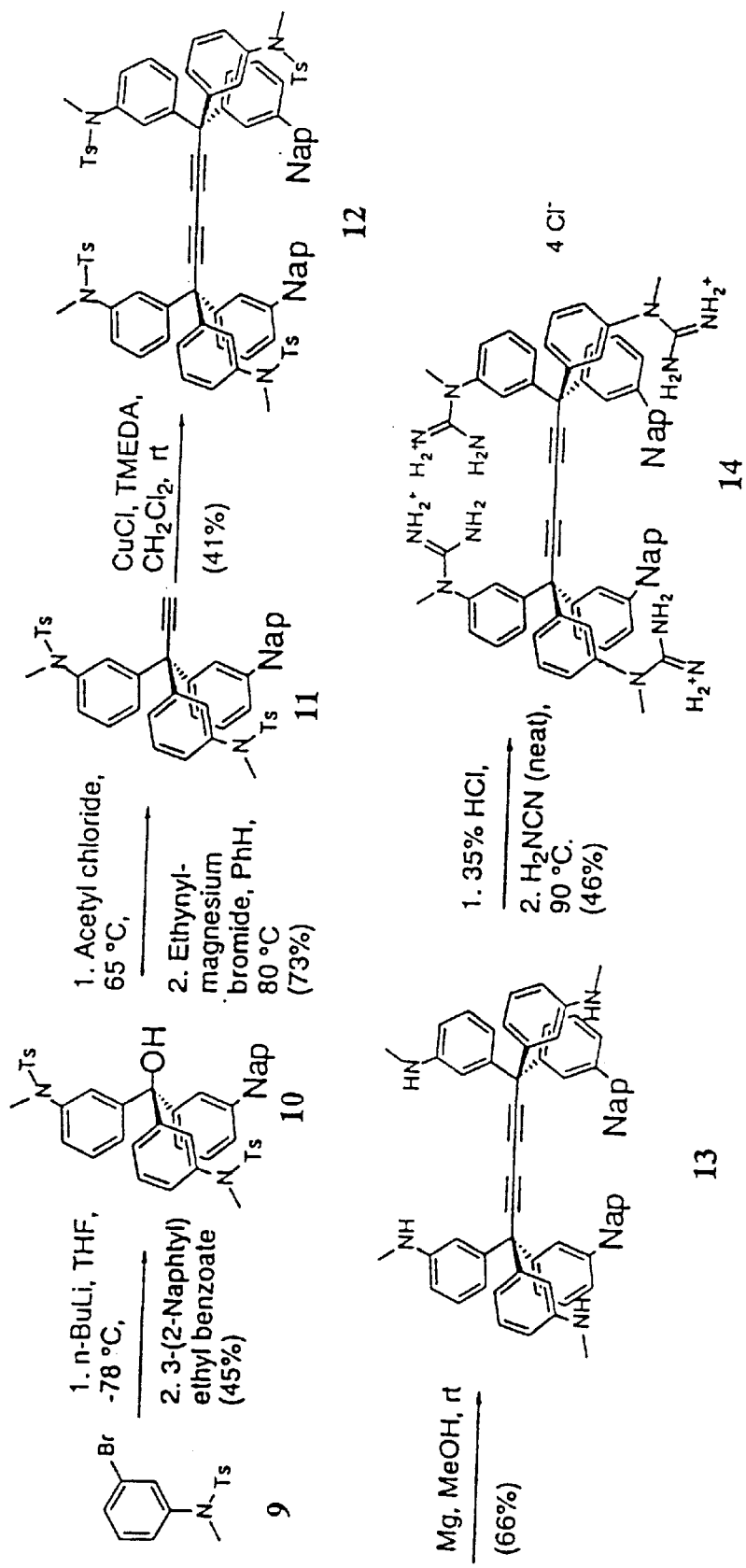
FIG. 5 shows the synthesis of 3-(2-Naphthyl)-3',3"-(N-guanidino-N-methyl)-bistrityl bisacetylene (Compound 14).

Synthesis of 3-(2-Naphthyl)-3',3"-(N-guanidino-N-methyl)-bistrityl Bisacetylene 3-(2-Naphthyl)-3',3"-(N-guanidino-N-methyl)-bistrityl bisacetylene was synthesized according steps A–F as described below and shown in FIG. 5.

A. Synthesis of 3-Bromo-1-(N-methyl-N-tosyl) aniline (Compound 9): 3-Bromoaniline (15 mL, 0.14 mol) was dissolved in pyridine (200 mL). The solution was cooled to 0° C. Tosyl chloride (27.6 g, 0.14 mol) was added at such a rate as to keep the reaction temperature from going above 5° C. After tosyl chloride addition was complete, the reaction was allowed to come to room temperature and was stirred for 10 hours under Argon. The reaction mixture was poured into 1 L of H$_2$O and was extracted with 2×300 ml portions of Et$_2$O. The organic layers were combined and washed successively with 3×300 ml portions of a 1 N citric acid solution, 2×300 ml portions of saturated aqueous NH$_4$CL and 300 ml H$_2$O. The organic layer was dried over NgSO$_4$, filtered and the solvent was removed. The crude material was recrystalized from 80 ml of CHCl$_3$ to obtain a total of 35.4 g (78%) of pure N-tosylated 3-bromoaniline. The 3-bromo-1-(N-tosyl) aniline (35.4 g, 0.10 mol) was dissolved in 1 L of EtOH. To this solution was added NaOH (4.33 g, 0.10 mol). Once the NaOH had dissolved, MeI (8.8 ml, 0.10 mol) was added via syringe. The reaction was allowed to stir at room temperature for 4 hours before adding an additional 8.8 ml of MeI. The reaction was allowed to stir for 10 hours. An additional 8.8 ml of MeI was added. Once the reaction was complete (followed by TLC), the solvent was removed. The resulting white solid was treated with 500 ml of EtOAc and 750 ml of saturated aqueous NH$_4$Cl. The aqueous layer was extracted with an additional 500 ml of EtOAc. The organics were combined, dried over MgSO$_4$, filtered and concentrated. The crude material was purified by silica gel chromatography using CH$_2$Cl$_2$ as the only solvent. Chromatography yielded 11.3 g of unreacted starting material and 16.0 g (88% yield based on recovered starting material) of crystalline 3-bromo-1-(N-methyl-N-tosyl) aniline (Compound 9): $^1$H NMR (400 MHz, CDCl$_3$) d 7.43 (d, 2H, J=8.2 Hz), 7.39–7.38 (m, 1H), 7.26 (d, 2H, J=8.3 Hz), 7.24 (m, 1H), 7.17 (t, 1H, J=8.0 Hz), 7.07 (m, 1H), 3.13 (s, 3H), 2.42 (s, 3H); $^{13}$C NMR (400 MHz, CDCl$_3$) d 144.4, 143.4, 133.5, 130.7, 130.5, 129.9, 129.8, 128.3, 125.6, 122.5, 38.3, 21.9; MS (MALDI-TOF) m/z (M+H) 340.0013; exact mass calculated for C$_{14}$H$_{15}$BrNO$_2$S 340.0007.

B. 3-(2-Naphthyl)-3',3"-(N-methyl-N-tosyl)-trityl alcohol (Compound 10): 3-Bromo-1-(N-methyl-N-tosyl) aniline (Compound 9) (1.26 g, 3.7 mmol) was dissolved in 20 mL of freshly distilled THF. The solution was cooled to −78° C. before adding n-BuLi (1.63 mL, 4.1 mmol). The reaction was allowed to stir at −78° C. for 15 minutes before adding 3-(2-Naphthyl)-1-ethylbenzoate (Compound 4) (0.257 g, 0.93 mmol) dissolved in 2 mL of THF. The reaction was allowed warm to room temperature over 3 hours. The reaction was quenched at 0° C. with 50 mL saturated aqueous NH$_4$Cl. The aqueous layer was extracted with 2×50 mL portions of Et$_2$O. The organics were combined, dried over MgSO$_4$, filtered and concentrated. Following silica gel chromatography using Et$_2$O/hexanes (5% Et$_2$O) the trityl alcohol Compound 10 (0.314 g, 45%) was obtained as a white, bubbly, non-recrystalizable solid: $^1$H NMR (400 MHz, CDCl$_3$) d 7.98 (s, 1H), 7.84–7.79 (m, 3H), 7.64 (m, 2H), 7.58 (s, 1H), 7.44–7.28 (m, 7H), 7.20 (m, 2H), 7.14–7.08 (m, 5H), 7.02 (m, 6H), 3.32 (brs, 1H, alcohol OH), 3.07 (s, 6H), 2.26 (s, 6H); $^{13}$C (200 MHz, CDCl$_3$) d 144.3, 146.5, 143.4, 141.3, 138.0, 133.5, 133.1, 132.5, 129.2, 128.4, 128.3, 128.1, 127.6, 127.5, 126.7, 126.2, 126.0, 125.8, 125.4, 125.3, 81.4, 37.8, 21.3; MS (MALDI-TOF) m/z (M+Na$^+$) 775.2244; exact mass calculated for C$_{45}$H$_{40}$N$_2$O$_5$S$_2$Na 775.2276.

C. Synthesis of 3-(2-Naphthyl)-3',3"-(N-methyl-N-tosyl)-trityl acetylene (Compound 11): 3-(2-Naphthyl)-3',3"-(N-methyl-N-tosyl)-trityl alcohol Compound 10 (2.59 g, 3.44 mmol) was dissolved in acetyl chloride (30 mL, 424 mmol) in a flask equipped with a drying tube. The solution was heated at reflux for 2.5 hours. The excess acetyl chloride was removed in vacuo. The resulting bubbly solid was dissolved in 200 mL of freshly distilled benzene. Ethynyl magnesium bromide (20.6 mL, 10.3 mmol, 0.5 M solution in THF) was added to this solution. The reaction was refluxed for 1.5 hours under argon. After cooling to room temperature, the reaction was poured into a saturated aqueous NH$_4$Cl solution. The aqueous layer was extracted with 3×200 mL Et$_2$O and 1×200 mL of CH$_2$Cl$_2$. The organics were combined, dried over MgSO$_4$ and concentrated. Following silica gel chromatography using a Et$_2$O/hexanes (80% Et$_2$O), 1.91 g (73%) of pure 3-(2-Naphthyl)-3',3"-(N-methyl-N-tosyl)-trityl acetylene (Compound 11) was obtained as a white non-recrystalizable solid: $^1$H NMR (400 MHz, CDCl$_3$) d 7.98 (s, 1H), 7.85 (t, 2H, J=8.7 H), 7.82 (m, 1H), 7.65 (dt, 2H, J=8.3, 1.4 Hz), 7.55 (m, 1H), 7.46 (m, 1H), 7.40 (t, 2H, J=7.8 Hz), 7.35 (d, 4H, J=8.2 Hz), 7.24 (t, 2H, J=7.9 Hz), 7.16–7.14 (m, 3H), 7.10–7.04 (m, 8H), 3.10 (s, 6H), 2.65 (s, 1H), 2.30 (s, 6H); $^{13}$C (400 MHz, CDCl$_3$) d 145.0, 143.4, 141.6, 133.3, 129.3, 128.6, 128.4, 128.2, 127.9, 127.9, 127.7, 127.5, 127.3, 126.3, 126.2, 126.0, 125.9, 125.4, 125.3, 88.5, 55.2, 38.0, 21.4; MS (MALDI-TOF), m/z (M+Na$^+$) 783.2345; exact mass calculated for C$_{47}$H$_{40}$N$_2$O$_4$S$_2$Na 783.2327.

D. Synthesis of 3-Naphthyl-3',3"-(N-methyl-N-tosyl)-bistrityl bisacetylene (Compound 12): Under an atmosphere of argon, 3-(2-Naphthyl)-3',3"-(N-methyl-N-tosyl)-trityl acetylene (Compound 11) (0.75 g, 0.98 mmol) was dissolved in 6 mL of CH$_2$Cl$_2$. To this solution, CuCl (2.55 g, 25.8 mmol) was added. Before adding TMEDA (3.8 mL, 25.2 mmol) the solution was cooled to 0° C. The reaction was allowed to come to room temperature. The reaction flask was flushed with O$_2$ and the flask was equipped with a drying tube. The reaction was allowed to stir at room temperature for 12 hours. The reaction was diluted with 40 mL CH$_2$Cl$_2$ and treated with saturated aqueous NH$_4$OH to remove the excess CuCl. The aqueous layer was extracted with 3×40 mL portions of CH$_2$Cl$_2$. The organics were combined and washed with brine, water, dried over MgSO$_4$, filtered and concentrated. Following silica gel chromatography using a CH$_2$Cl$_2$/Et$_2$O (3% Et$_2$O), 0.309 g (41%) of 3-(2-Naphthyl)-3',3"-(N-methyl-N-tosyl)-bistrityl bisacetylene (Compound 12) was obtained as a white non-recrystalizable solid: $^1$H NMR (400 MHz, CDCl$_3$) d 7.96 (s, 2H), 7.85–7.79 (m, 6H), 7.64 (m, 4 H), 7.46–7.39 (m, 8H), 7.31 (d, 8H J=8.2 Hz), 7.24–7.20 (m, 9H), 7.05–6.97 (m, 17H); $^{13}$C (400 MHz, CDCl$_3$) d 144.5, 143.5, 141.6, 138.0, 138.0, 133.5, 133.3, 129.3, 128.6, 128.5, 128.2, 127.9, 127.8, 127.6, 127.5, 127.5, 126.3, 125.9, 125.4, 125.0, 83.9, 70.3, 56.1, 37.9, 21.4; MS (FAB) m/z (M+H$^+$) 1519.4817; exact mass calculated for C$_{94}$H$_{79}$N$_4$O$_8$S$_4$ 1519.4781.

E. Synthesis of 3-(2-Naphthyl)-3',3"-(N-methyl)-bistntyl bisacetylene (Compound 13): 3-(2-Naphthyl)-3',3"-(N-methyl-N-tosyl)-bistrityl bisacetylene (Compound 12) (0.309 g, 0.204 mmol) was suspended in 30 mL of MeOH. The compound was forced into solution by adding 15 mL of CH$_2$Cl$_2$. To this solution was added Mg turnings (0.98 g, 41 mmol). After a latent period of approximately 1 hour the reaction became vigorous and was cooled with an ice-water bath. The reaction was completed after approximately 4 hours total time, when the magnesium turnings were completely dissolved. The reaction was then treated with 100 mL of a 50% aqueous acetic acid solution. The layers were separated and the aqueous layer was extracted with 2×100 mL portions of Et$_2$O. The organics were combined, dried over MgSO$_4$, filtered and concentrated. The residue was taken up in 50 mL of CH$_2$Cl$_2$ and 50 mL of water was added. The aqueous layer was made basic with solid NaHCO$_3$. The organic layer was washed once more with saturated aqueous NaHCO$_3$. The organic layer was then dried over MgSO$_4$, filtered and concentrated. Following silica gel chromatography using CH$_2$Cl$_2$/Et$_2$O/Et$_3$N (2% Et$_2$O, 2% Et$_3$N), 0.12 g (66%) of pure 3-(2-Naphthyl)-3',3"-(N-methyl)-bistrityl bisacetylene (Compound 13) was obtained as a white non-recrystalizable solid: $^1$H NMR (400 MHz, CDCl$_3$) d 7.94 (s, 2H), 7.80 (m, 6H), 7.72 (s, 2H), 7.63 (m, 2H), 7.60 (m, 2H), 7.44 (m, 4H), 7.36 (m, 2H), 7.24 (m, 2H), 7.11 (m, 4H), 6.64–6.59 (m, 8H), 6.49 (m, 4H), 3.65 (br s, 4H), 2.72 (s, 12H); $^{13}$C (400 MHz, CDCl$_3$) d 149.0, 145.5, 145.4, 140.5, 138.4, 133.6, 132.5, 128.8, 128.3, 128.3, 128.2, 127.5, 126.1, 125.9, 125.8, 125.6, 118.6, 114.4, 110.3, 84.6, 70.0, 56.5, 30.7; MS (CI), m/z (M+H$^+$) 903.4405; exact mass calculated for C$_{66}$H$_{55}$N$_4$ 903.4427.

F. Synthesis of 3-(2-Naphthyl)-3',3"-(N-guanidino-N-methyl)-bistrityl bisacetylene (Compound 14): 3-Naphthyl-3',3"-(N-methyl)-bistrityl bisacetylene (Compound 13) (0.057 g, 0.054 mmol) was treated with 0.5 mL of 35% aqueous HCl. The water was removed from the sample in vacuo. Cyanamid (0.311 g, 7.39 mmol) was added to the flask. The cyanamid was melted and the reaction temperature was brought up to 90° C. The reaction was heated for 6 hours at 90° C. By this time the reaction had solidified. This solid (Compound 14) was dissolved in MeOH (10 mL). One half of this solution was taken and chromatographed by means of gel filtration chromatography (Sepahdex CM-25, NH$_4$HCO$_3$ buffer, 0.7–1 M). However, the compound never eluted from the column even at the highest concentration of buffer (1 M). The remaining 5 mL of the MeOH solution of Compound 14 was evaporated to dryness. The solid thus obtained was treated with 20 mL of acetone to wash away byproducts from the reaction. The product Compound 14 (0.030 g, 46% yield) was obtained as an off-white solid which was used without further purification: $^1$H NMR (200 MHz, DMSO) d 8.06 (s), 8.03–7.83 (m), 7.82–6.49 (m), 3.18 (s).

Example 4

Fluorescence Titrations of Compound 14 with Phthalic Acid Dipotassium Salt

Figure 6:
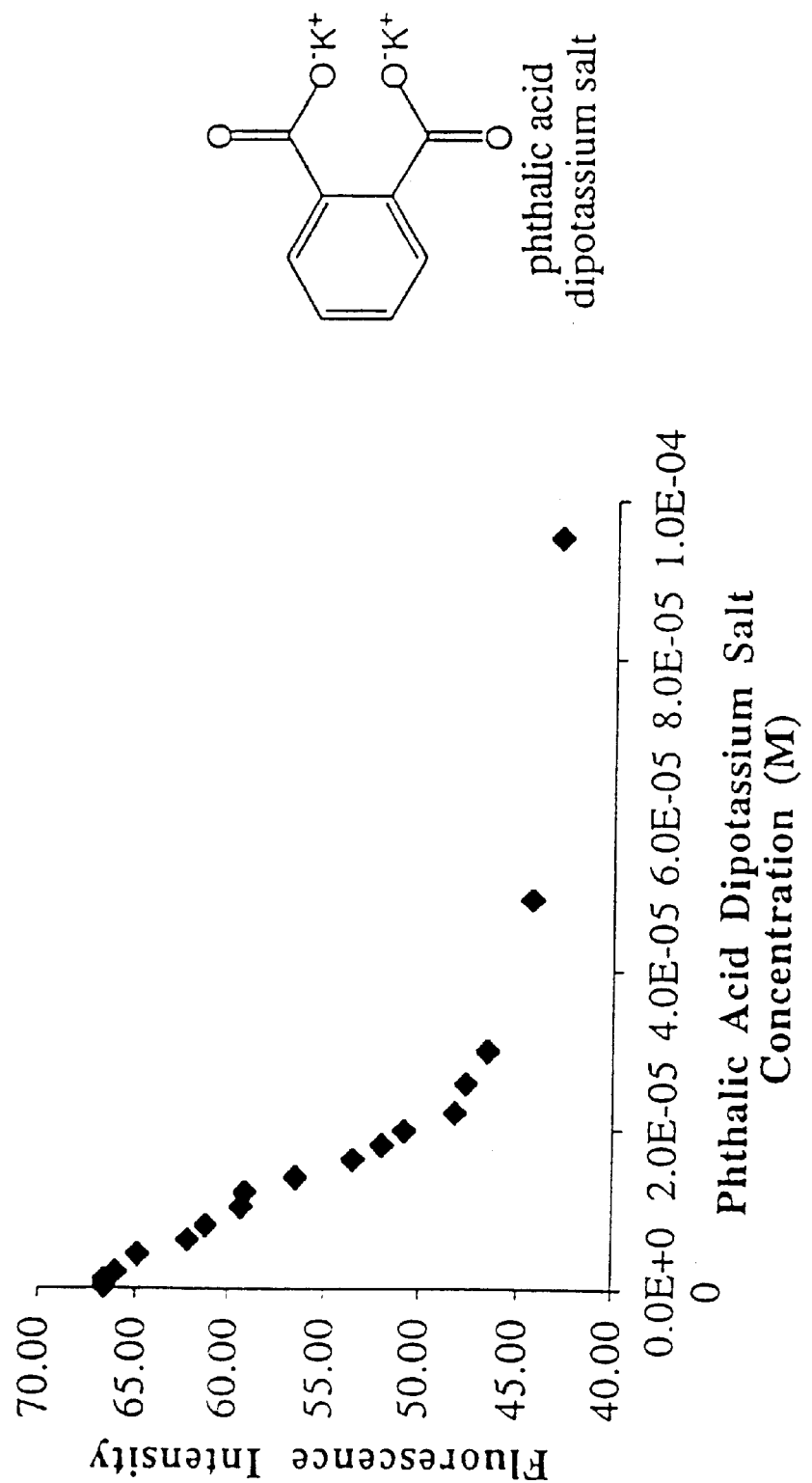
FIG. 6 is a graph depicting the titration curve of Compound 14 with phthalic acid dipotassium salt.
Figure 7:
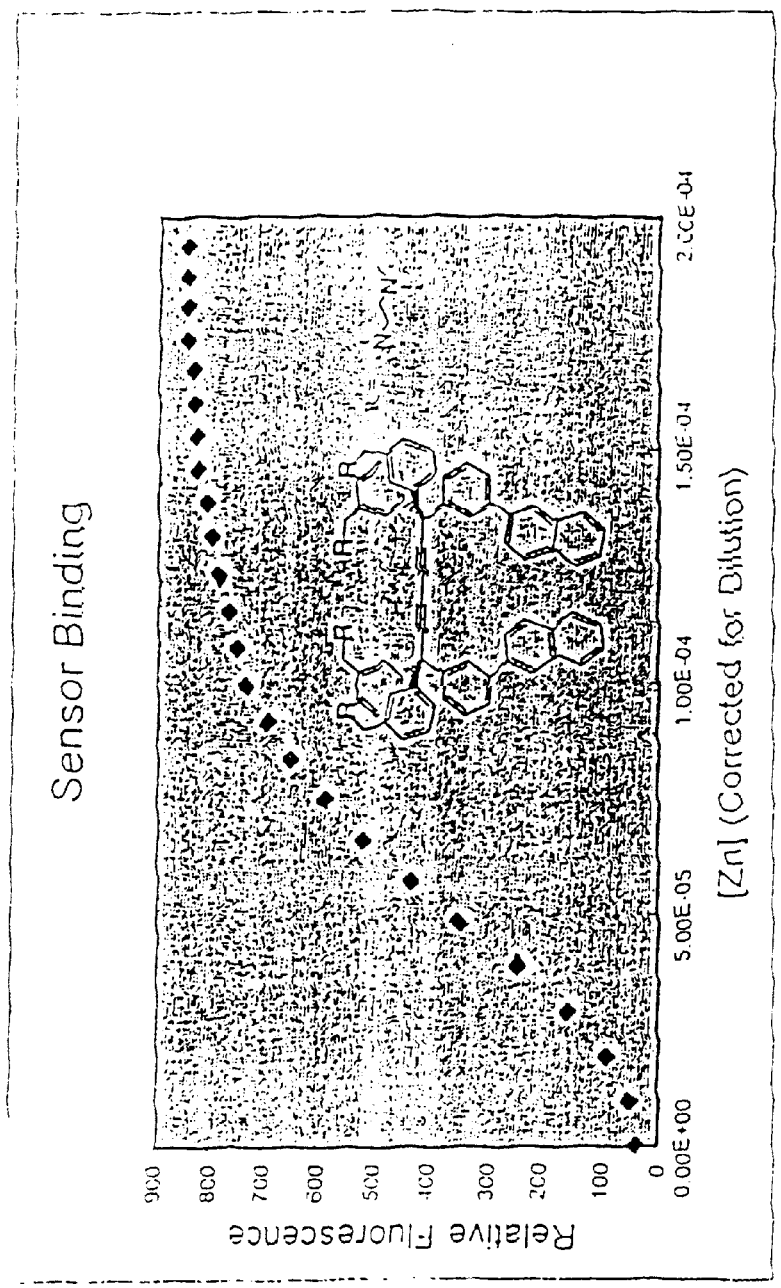
FIG. 7 is a graph depicting the titration curve of Compound 8 with zinc ions (zinc nitrate) in acetonitrile.
Figure 8:
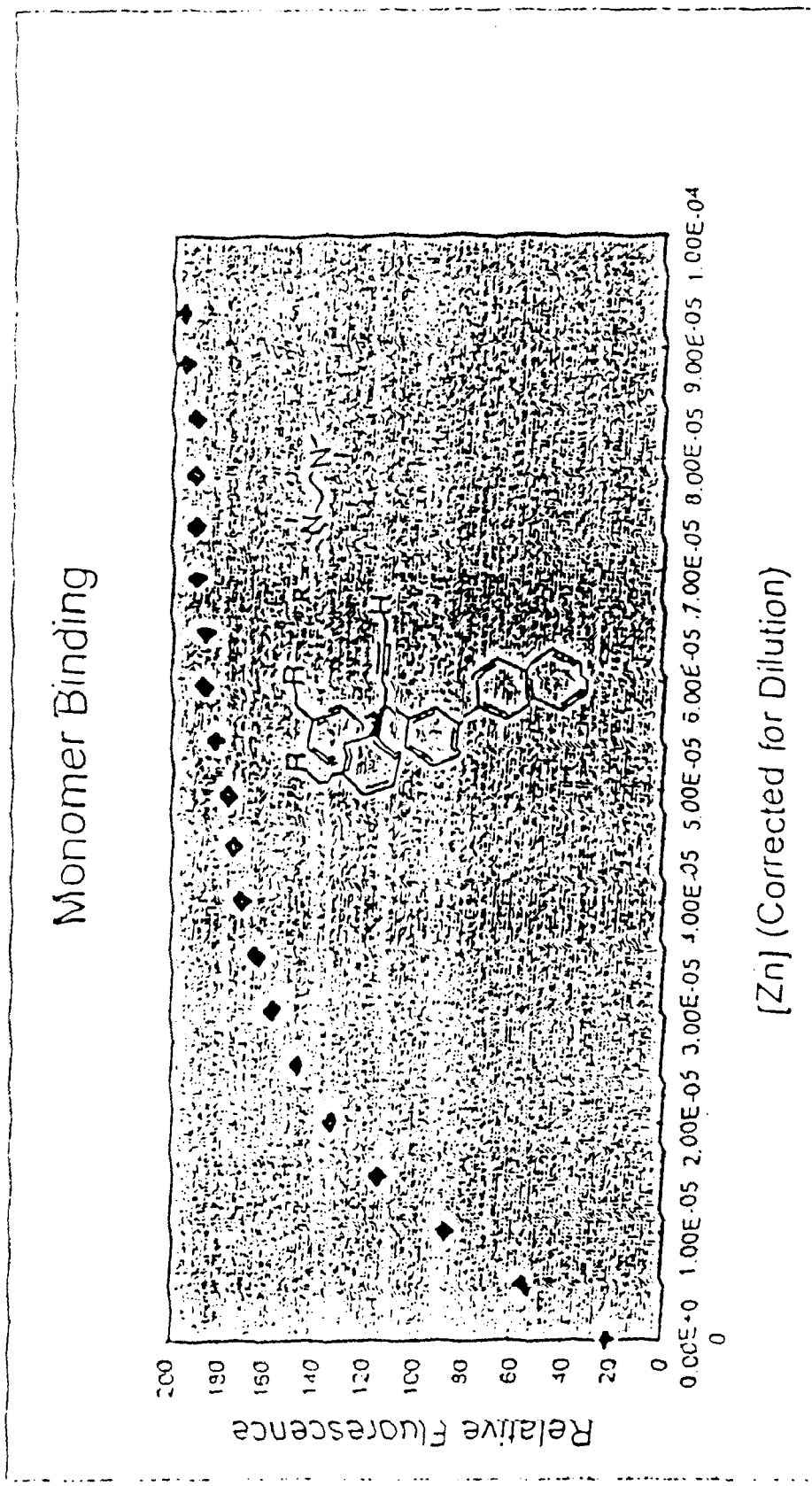
FIG. 8 is a graph depicting the titration curve of a molecule consisting of one half of Compound 8 (i.e., a monomer) with zinc ions (zinc nitrate) in acetonitrile.
Figure 9:
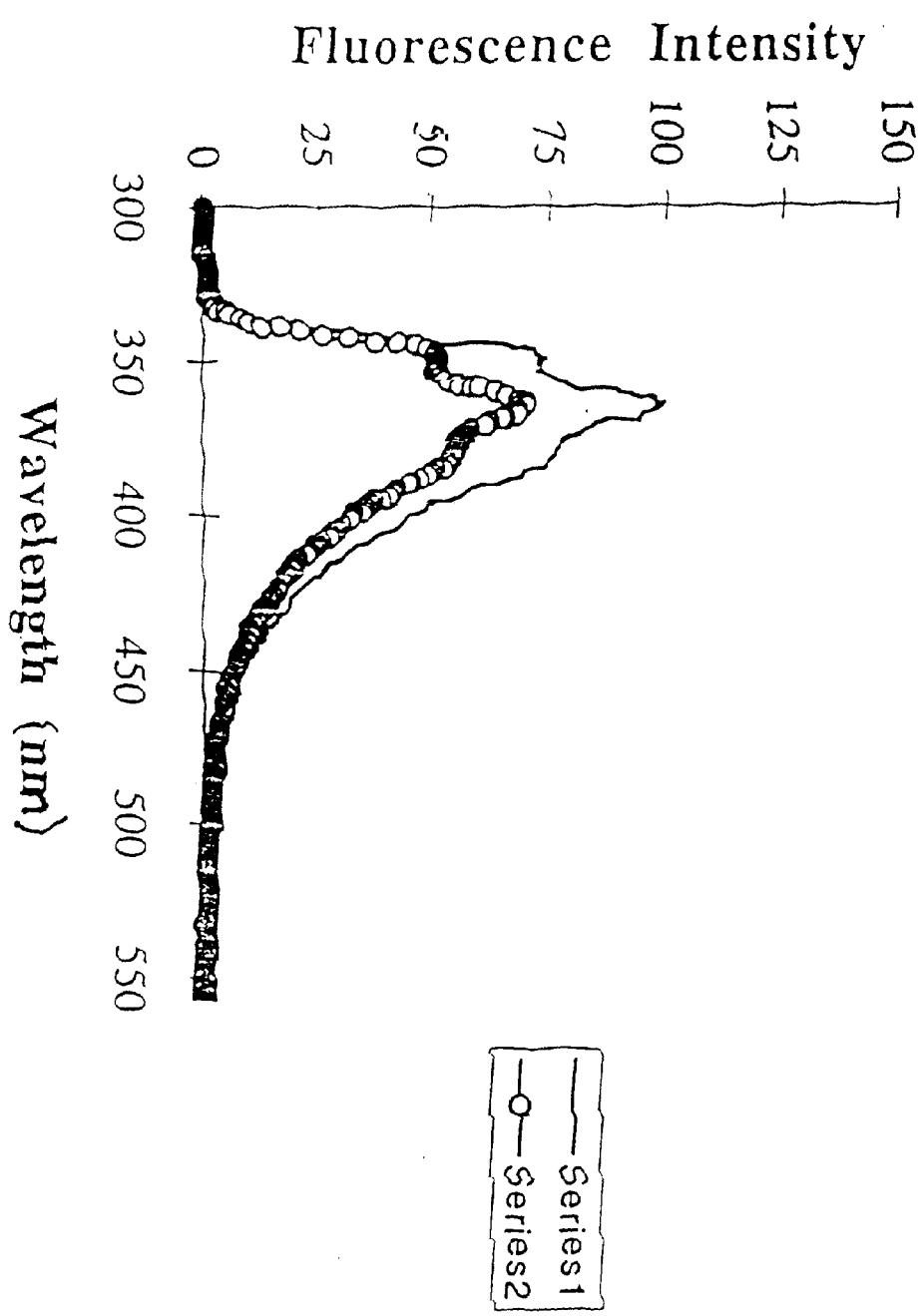
FIG. 9 is a graph that shows the effect of Phthalic Acid Dipotassium Salt on the fluorescence intensity of Compound 14 (Series 1=no dicarboxylate; Series 2=dicarboxylate added).

Referring to FIGS. 6 and 9, a 2.4×10$^{-3}$ stock solution of Compound 14 was made by dissolving 30 mg of Compound 14 in 10 mL of MeOH. A 100 µl aliquot of the stock solution was diluted to 10 mL with a Tris buffer solution (pH=8.00)

to make a 2.4×10⁻⁵ M aqueous solution of Compound 14. A 2 mL aliquot of this solution was placed in a quartz fluorescence cell and a fluorescence spectrum of Compound 14 was taken (see FIG. 9, Series 1). A 2×10⁻³ M solution of phthalic acid dipotassium salt was titrated into the fluorescence cell. The excitation wavelength was 290 nm. The decrease in fluorescence at 363 nm was recorded after each addition of dicarboxylate showing that compound 14 acts as a chemosensor. The data also indicate that compound 14 binds the analyte in a cooperative fashion. A representative curve is shown as Series 2 in FIG. 9 after a total of 40 μl of dicarboxylate solution (4×10⁻⁵ M) had been added to the fluorescence cell.

Example 5

Figure 16:
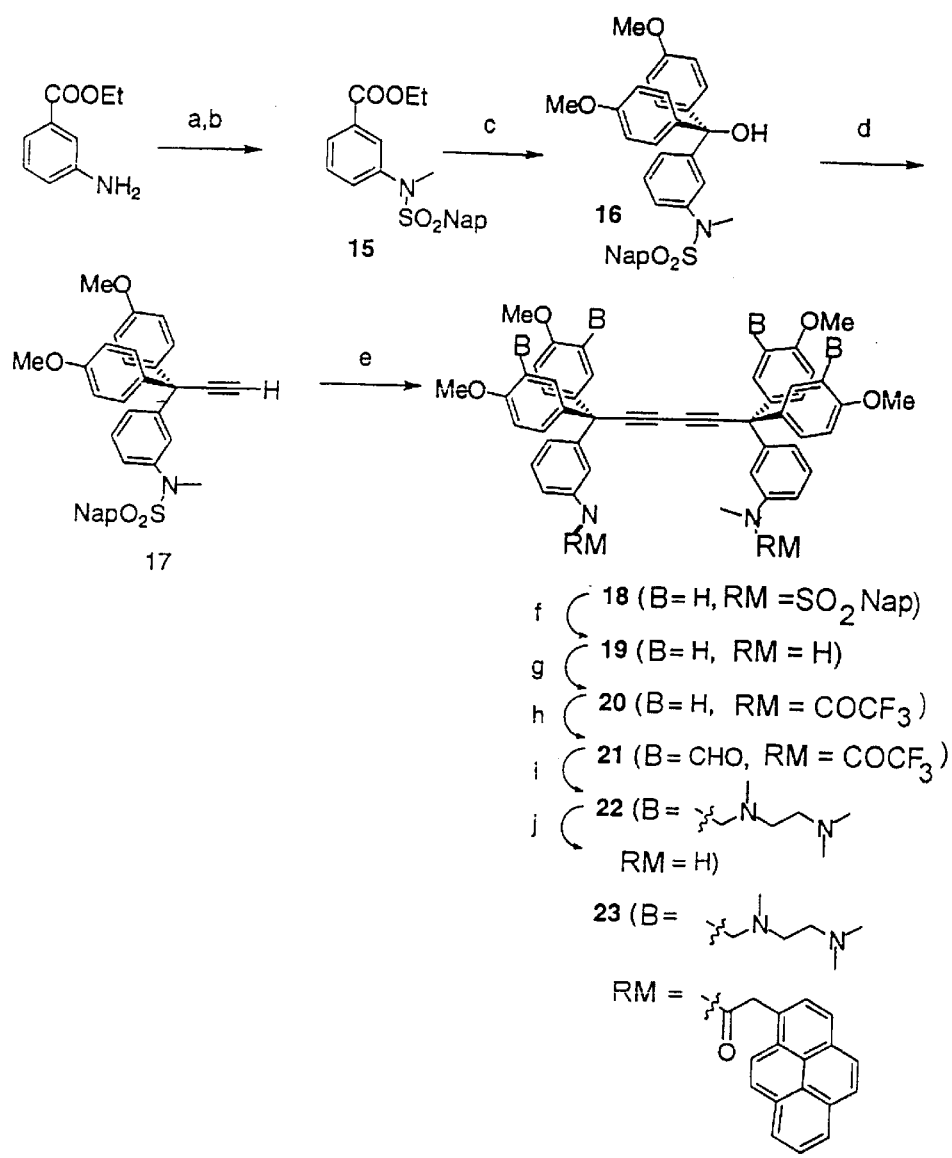
FIG. 16 shows the synthesis of 1,1,6,6-tetrakis(4-methoxy-3-(((2-dimethylaminoethyl)-methyl-amino)-methyl)phenyl)-1,6-bis(N-methyl-3-aminophenyl-N-(2-(1-pyrenyl)-acetyl)-2,4-hexadiyne (Compound 23). (a) 2-naphthalene sulfonyl chloride, DMAP, Pyr. (95%); (b) MeI, NaOH, EtOH (75%); (c) 4-bromoanisole/n-BuLi, THF (94%); (d) I) AcCl II) ethynyl magnesium bromide, PhH (85%); (e) CuCl, N-methylpyrrolidine, $O_2$, DCM (74%); (f) Mg(0), MeOH, DCM (100%); (g) $(F_3CCO)_2O$, THF (98%); (h) $Cl_2CHOCH_3$, $TiCl_4$, DCM (99%); (i) I) trimethyl ethylenediamine, AcOH, EtOH, Mol. Sieves (4 Å) II) $NaBH_3CN$ III) $NH_3$, MeOH (93%); j) I-pyrenylacetic acid, DIC THF (48%).

Synthesis of 1,1,6,6-Tetrakis(4-methoxy-3-(((2-dimethylamino-ethyl)-methyl-amino)-methyl)phenyl)-1,6-bis(N-methyl-3-aminophenyl-N-(2-(1-pyrenyl)-acetyl)-2,4-hexadiyne 1,1,6,6-tetrakis(4-methoxy-3-(((2-dimethylamino-ethyl)-methyl-amino)-methyl)phenyl)-1,6-bis(N-methyl-3-aminophenyl-N-(2-(1-pyrenyl)-acetyl)-2,4-hexadiyne was synthesized according to steps A–G described below and shown in FIG. 16.

A. Synthesis of N-methyl-N-(2-naphthalenesulfonyl) ethyl-3-aminobenzoate (Compound 15): A solution of pyridine (1 L), dimethylaminopyridine (1.22 g, 10 mmol), ethyl-3-aminobenzoate (14.9 ml, 100 mmol), and 2-naphthalenesulfonyl chloride (23.8 g, 105 mmol) was stirred at 75° C. for 18 hours. The solvent was removed in vacuo, and the resulting residue was purified using flash chromatography (EtOAc/$CH_2Cl_2$, 10:90). N-(2-sulfonylnaphthalene) ethyl-3-aminobenzoate was isolated as a white crystalline solid (35.5 g, 99.9 mmol, 100% yield). mp 122–124° C.; ¹H NMR (300 MHz) d 1.32 (t, J=7.1 Hz, 3H), 4.33 (q, J=7.1 Hz, 2H), 7.28 (t, J=7.9 Hz, 1H), 7.46–7.61 (m, 3H), 7.73 (dt, J=1.2, 7.8 Hz, 1H), 7.71–7.86 (m, 6H), 8.41 (d, J=1.3 Hz, 1H); ¹³C NMR (100 MHz) d 14.2, 61.5, 122.1, 122.1, 125.2, 126.0, 127.6, 127.9, 129.0, 129.3, 129.4, 129.6, 131.5, 132.0, 134.9, 135.8, 137.1, 166.1; IR (neat) 3248, 3058, 2982, 2904, 1719, 1696, 1590, 1471, 1404, 1214, 1020, 961, 882, 755 cm⁻¹; HRMS calculated for $C_{19}H_{18}NO_4S$ (M+H⁺): 356.0957, found: 356.0953.

A solution of EtOH (abs., 1 L) and N-(2-naphthalenesulfonyl) ethyl-3-aminobenzoate (35.5 g, 99.9 mmol) was warmed to 60° C. NaOH (6.0 g, 149.9 mmol) was added, and the reaction was stirred until all of the solid had dissolved. Methyl iodide (9.33 ml, 150 mmol) was added, and the resulting mixture was stirred at 60° for 22 hours. The solvent was removed in vacuo, and the resulting residue was dissolved in $CH_2Cl_2$ and washed with saturated $NH_4Cl$. The aqueous layer was extracted with $CH_2Cl_2$ (3×250 ml), and the organic phase was dried over $MgSO_4$. After removal of the $CH_2Cl_2$, the resulting residue was purified using flash chromatography ($CH_2Cl_2$). The title compound 15 was isolated as a yellow amorphous solid (27.5 g, 74.4 mmol, 75% yield). ¹H NMR (400 MHz) d 1.30 (t, J=7.2 Hz, 3H), 3.24 (s, 3H), 4.30 (q, J=7.1 Hz, 2H), 7.36–7.41, (m, 2H), 7.73 (dd, J=1.8, 6.9 Hz, 1H), 7.56–7.66 (m, 2H), 7.72 (s, 1H), 7.87–7.90 (m, 3H), 7.94–7.97 (m, 1H), 8.18 (d, J=1.2 Hz, 1H); ¹³C NMR (100 MHz) d 12.3, 36.3, 59.3, 121.1, 125.3, 125.7, 126.1, 126.6, 127.1, 127.1, 127.2, 127.4, 127.4, 129.5, 129.6, 130.1, 131.5, 133.1, 140.0, 163.8; IR (neat) 3057, 2980, 1719, 1586, 1443, 1349, 1286, 1240, 1072, 927, 759 cm⁻¹; HRMS calculated for $C_{20}H_{19}NO_4SNa$ (M+Na⁺): 392.0932, found: 392.0950.

B. Synthesis of Bis(4-methoxyphenyl)-3-N-methyl-N-(2-sulfonylnaphthyl)aminophenyl methanol (Compound 16): n-BuLi (126 ml, 201 mmol, 1.6M in hexanes) was added to a stirred solution of THF (2.2 L) and 4-bromoanisole (27.9 ml, 223 mmol) at −78° C. The reaction mixture was allowed to stir for 20 min., followed by addition of compound 15 (27.5 g, 74.4 mmol) in THF (250 ml, −78° C.). The reaction mixture was allowed to warm to 0° C., and quenched with $NH_4Cl$. The aqueous layer was extracted with $CH_2Cl_2$ (3×250 ml). The organic layer was dried over $MgSO_4$, and the solvent removed in vacuo. Flash chromatography (EtOAc/Hex, 35:65) afforded the title compound 16 as a white solid (37.6 g, 69.7 mmol, 94% yield). mp 61–62° C.; ¹H NMR (400 MHz) d 2.61 (s, 1H), 3.14 (s, 3H), 3.76 (s, 6H), 6.71 (bd, J=8.9 Hz, 4H), 6.87 (t, J=1.9 Hz, 1H), 7.01 (bd, J=8.8 Hz, 4H),7.17–7.28 (m, 3H), 7.39 (dd, J==1.8, 6.0 Hz, 1H), 7.58–7.64 (m, 2H), 7.74 (d, J=8.7 Hz, 1H), 7.84 (d, J=8.1 Hz, 1H), 7.88 (d, J=8.1 Hz, 1H), 8.12 (s, 1H); ¹³C NMR (100 MHz) d 38.6, 55.7, 81.4, 113.6, 123.4, 125.4, 126.4, 127.1, 127.6, 128.1, 128.6, 129.0, 129.0, 129.1, 129.3, 129.5, 132.4, 134.0, 135.2, 139.2, 141.5, 148.7, 159.1; IR (neat) 3507, 3058, 3001, 2954, 2836, 1607, 1508, 1347, 1250, 1175, 1033, 828, 734 cm⁻¹; HRMS calculated for $C_{32}H_{29}NO_5SNa$ (M+Na⁺): 562.1664, found: 562.1676.

C. Synthesis of 3,3-bis(4-methoxyphenyl)-3-N-methyl-N-(2-naphthalenesulfonyl)-3-aminophenyl)-1-propyne (Compound 17): A solution of compound 16 (18 g, 33.4 mmol) and acetyl chloride (180 ml) was stirred at room temperature for 2 hours. The acetyl chloride was removed in vacuo, and the resulting solid was carefully dried under high vacuum. The solid was dissolved in benzene (1 L). The solution was sparged with a steady stream of argon for 15 minutes. Ethynylmagnesium bromide (334 ml, 167 mmol, 0.5M in THF) was added to the reaction, and stirred at room temperature (room temperature (rt) for 1.5 hours. The reaction was quenched with saturated $NH_4Cl$, and the aqueous layer was extracted with $CH_2Cl_2$ (3×125 ml). The organic layer was then dried over $MgSO_4$, and the solvent removed in vacuo. Flash chromatography (EtOAc/Hex, 30:70) afforded the title compound 17 as an amorphous solid (15.5 g, 28.3 mmol, 85% yield). ¹H NMR (400 MHz) d 2.39 (s, 1H), 3.12 (s, 3H), 3.75 (s, 6H), 6.68 (bd, J=8.9 Hz, 4H), 6.75 (t, J=1.8 Hz, 1H), 6.98 (bd, J=8.8 Hz, 4H), 7.18 (dt, J=1.8, 7.1 Hz, 1H), 7.22–7.28 (m, 2H), 7.43 (dd, J=1.7, 8.6 Hz, 1H), 7.56–7.66 (m, 2H), 7.78 (d, J=8.7 Hz, 1H), 7.87 (t, J=8.8 Hz, 2H), 8.12 (s, 1H); ¹³C NMR (100 MHz) d 38.7, 54.3, 55.6, 73.6, 89.8, 113.7, 123.6, 126.5, 126.8, 127.8, 128.3, 128.5, 128.9, 129.2, 129.3, 129.5, 129.8, 130.3, 132.4, 134.0, 135.2, 136.9, 141.6, 146.8, 158.8; IR (neat) 3289, 3057, 2932, 2835, 1605, 1507, 1347, 1251, 1177, 1033, 826 cm⁻¹; HRMS calculated for $C_{34}H_{19}NO_4SNa$ (M+Na⁺): 570.1715, found: 570.1714.

D. Synthesis of 1,1,6,6-tetrakis(4-methoxyphenyl)-1,6-bis(N-methyl-N-(2-napthalenesulfonyl)-3-aminophenyl))-2,4-hexadiyne (Compound 18): Copper (I) chloride (28.0 g, 283 mmol) was added to a stirred solution of $CH_2Cl_2$ (290 ml) and compound 17 (15.5 g, 28.3 mmol). N-methylpyrrolidine (59 ml, 566 mmol) was added in a dropwise fashion. The solution was stirred at ambient temperature for 2.5 hours with a steady stream of bubbling $O_2$. The reaction mixture was filtered through a short silica column with EtOAc, and the solvent removed in vacuo. The residue was purified via flash chromatography (EtOAc/Hex, 40:60), and the title compound 18 was isolated as a white amorphous solid (11.4 g, 20.9 mmol, 74% yield). ¹H NMR (400 MHz) d 3.09 (s, 6H), 3.74 (s, 12H), 6.63–6.68 (m, 10H), 6.94 (bd, J=8.8 Hz, 8H), 7.17–7.28 (m, 7H), 7.40 (dd, J=2.0, 8.5 Hz, 2H), 7.53–7.62 (m, 4H), 7.74 (d, J=8.5 Hz, 2H), 7.79–7.84 (m, 4H), 8.10 (s, 2H); $^{13}$C NMR (100 MHz) d 36.2, 52.7, 53.3, 67.7, 82.3, 111.4, 121.1, 124.1, 124.2, 125.4, 125.9, 126.3, 126.7, 126.8, 126.9, 127.1, 127.3, 127.9, 130.0, 131.6, 132.8, 134.0, 139.2, 144.0, 156.5; IR (neat) 3010, 2932, 2836, 1605, 1057, 1348, 1177, 1072, 1033, 825 cm$^{-1}$; HRMS calculated for $C_{68}H_{56}N_2O_8S_2Na$ (M+Na$^+$): 1115.3376, found: 1115.3395.

E. Synthesis of 1,1,6,6-tetrakis(4-methoxyphenyl)-1,6-bis(N-methyl-N-trifluoroacetyl-3-aminophenyl))-2,4-hexadiyne (Compound 20): Compound 18 (4.0 g, 3.7 mmol) and Mg turnings (17.8 g, 732 mmol) were added to a stirred solution of CH$_2$Cl$_2$ (500 ml) and MeOH (500 ml). After 30 min., the reaction began to reflux. The solution was then stirred at ambient temperature for 24 hours. The solvent was removed in vacuo, and the residue was brought up in 50% AcOH (aq.), and extracted with CH$_2$Cl$_2$ (3×200 ml) and dried over MgSO$_4$. After removal of the solvent in vacuo, the residue was purified via flash chromatography (EtOAc/Hex, 40:60), and 1,1,6,6-tetrakis(4-methoxyphenyl)-1,6-bis(N-methyl-3-aminophenyl))-2,4-hexadiyne (19) was isolated as a white solid (2.60 g, 3.7 mmol, 100% yield). mp 123–125° C.; $^1$H NMR (360 MHz) d 2.77 (s, 6H), 3.79 (s, 12H), 6.49–6.53 (m, 6H), 6.80 (d, J=8.5 Hz, 8H), 7.10 (t, J=7.8 Hz, 2H), 7.15 (d, J=9.1 Hz, 8H); $^{13}$C NMR (100 MHz) d 31.1, 55.3, 55.7, 69.9, 84.9, 110.6, 113.6, 114.5, 118.8, 129.2, 130.6, 137.5, 146.3, 149.4, 158.7; IR (neat) 3416, 3000, 2953, 2835, 1605, 1507, 1298, 1251, 1177, 1033, 909, 828 cm$^{-1}$; HRMS calculated for $C_{48}H_{45}N_2O_4$ (M+H$^+$): 713.3379, found: 713.3404.

Trifluoroacetic anhydride (1.29 ml, 9.1 mmol) was added to a stirred solution of THF (20 ml) and compound 19 (649 mg, 0.91 mmol) at 0° C. The solution was warmed to ambient temperature and quenched with water (20 ml). The aqueous layer was extracted with CH$_2$Cl$_2$ (3×10 ml), and the collected organic layers were dried over MgSO$_4$. After removal of the solvent in vacuo, the residue was filtered through a silica plug (EtOAc/Hex, 40:60), and the title compound 20 was isolated as an amorphous red solid (808 mg, 0.89 mmol, 98% yield). $^1$H NMR (300 MHz) d 3.30 (s, 6H), 3.80 (s, 12H), 6.84 (d, J=8.8 Hz, 8H), 7.08–7.16 (m, 12H), 7.32–7.40 (m, 4H); $^{13}$C NMR (75 MHz) d 29.7, 54.8, 55.3, 69.7, 84.2, 113.6, 116.3 (q, J=285 Hz), 125.8, 128.0, 129.3, 129.7, 130.0, 135.9, 140.3, 147.2, 157.0 (q, J=35.8 Hz), 158.7; IR (neat) 3385, 3010, 2934, 1698, 1605, 1508, 1253, 1205, 1155, 1034, 910, 829 cm$^{31}$ $^1$; HRMS calculated for $C_{52}H_{42}N_2O_6F_6$ (M+Na$^+$): 927.2845, found: 927.2874.

F. Synthesis of 1,1,6,6-tetrakis(4-methoxy-3-formylphenyl)-1,6-bis(N-methyl-N-trifluoroacetyl-3-aminophenyl)-2,4-hexadiyne (Compound 21): 1,1-dichloromethylmethyl ether (0.24 ml, 2.64 mmol) was added to a stirred solution of CH$_2$Cl$_2$ (15 ml) and compound 20 (300 mg, 0.33 mmol) at 0° C. TiCl$_4$ (3.6 ml, 1.0 M in CH$_2$Cl$_2$, 3.63 mmol) was added in a dropwise fashion to the reaction. The reaction was allowed to warm to ambient temperature over a period of 45 minutes. The mixture was slowly poured over ice, and the aqueous layer was extracted with CH$_2$Cl$_2$ (3×20 ml). The organic layer was dried over MgSO$_4$, and the solvent removed in vacuo. The resulting residue was purified via flash chromatography (EtOAc/Hex, 70:30) to yield the title compound 21 as a white amorphous solid (332 mg, 0.326 mmol, 99% yield). $^1$H NMR (360 MHz) d 3.32 (s, 6H), 3.95 (s, 12H), 6.99 (d, J=9.0 Hz, 4H), 7.09 (s, 2H), Hz, 2H), 7.28 (d, J=8.0 Hz, 2H), 7.38–7.47 (m, 6H), 7.58 (d, J=2.7 Hz, 4H), 10.41 (s, 4H); $^{13}$C NMR (90 MHz) d 39.7, 54.7, 55.9, 70.5, 83.7, 112.1, 116.3 (q, J=288 Hz), 124.4, 126.5, 128.0, 128.4, 129.3, 129.8, 135.5, 136.2, 140.7, 145.5, 156.8 (q, J=35.6 Hz), 161.2, 189.3; IR (neat) 3020, 2944, 2867, 1690, 1686, 1604, 1492, 1283, 1257, 1204, 1155, 1024, 756 cm$^{31}$ $^1$; HRMS calculated for $C_{56}H_{42}N_2O_{10}F_6Na$ (M+Na$^{30}$): 1039.2641, found: 1039.2677.

G. Synthesis of 1,1,6,6-tetrakis(4-methoxy-3-(((2-dimethylamino-ethyl)-methyl-amino)-methyl)phenyl)-1,6-bis(N-methyl-3-aminophenyl-N-(2-(1-pyrenyl)-acetyl)-2,4-hexadiyne (Compound 23): AcOH (2 ml, glacial) and 4 Å mol. sieves were added to a stirred solution of EtOH (abs., 2 ml,), compound 21 (500 mg, 0.49 mmol), and N,N,N'-trimethyl ethylenediamine (1.87 ml, 14.7 mmol). The reaction was stirred at ambient temperature for 4 hours. NaBH$_3$CN (616 mg, 9.8 mmol) was added to the solution, and the reaction was allowed to stir at ambient temperature for 14 hours. The reaction mixture was added to 10% HCl (50 ml) and allowed to stir for 15 minutes. The reaction was then made basic (pH 10) with 10M NaOH. The aqueous layer was extracted with CH$_2$Cl$_2$. The organic layer was dried over MgSO$_4$, and removed in vacuo. The resulting residue was placed in a sealed vessel with 10 ml of NH$_3$ in MeOH, and stirred at RT for 3 hours. The solvent was removed in vacuo, and the resulting residue was purified via flash chromatography (NH$_3$ sat. MeOH/CHCl$_3$, 10:90), and 1,1,6,6-tetrakis(4-methoxy-3-(((2-dimethylamino-ethyl)-methyl-amino)-methyl)phenyl)-1,6-bis(N-methyl-3-aminophenyl)-2,4-hexadiyne (Compound 22) was isolated as a yellow amorphous solid (533 mg, 0.46 mmol, 93% yield). $^1$H NMR (400 MHz) d 2.14 (s, 12H), 2.16 (s, 24H), 2.42–2.66 (m, 16H), 2.74 (s, 6H), 3.45 (d, J=12.6 Hz, 4H), 3.50 (d, J=13.1 Hz, 4H), 3.80 (s, 12H), 3.82 (bs, 2H), 6.54 (d, J=8.7 Hz, 4H), 6.74 (t, J=1.6 Hz, 2H), 6.86 (dd, J=2.5, 8.6 Hz, 4H), 6.45–6.54 (m, 6H), 6.73 (d, J=9.1 Hz, 4H), 7.05–7.09 (m, 6H), 7.13 (d, J=2.1 Hz, 4H); $^{13}$C NMR (100 MHz) d 31.1, 42.9, 46.2, 55.3, 55.8, 55.9, 56.7, 57.7, 69.9, 85.0, 110.1, 110.3, 114.6, 118.7, 126.2, 129.1, 132.5, 136.8, 146.4, 149.4, 157.1; IR (neat) 3266, 2942, 2814, 1604, 1496, 1463, 1251, 1112, 1031 cm$^{-1}$; HRMS calculated for $C_{72}H_{101}N_{10}O_4$ (M+H$^+$): 1169.8007 found: 1169.8016.

A mixture of 1-pyrene acetic acid (18 mg, 0.068 mmol), diisopropyl carbodiimide (11 μl, 0.068 mmol), and THF (1 ml) were stirred at ambient temperature for 3.5 hours. The reaction was then added to a flask containing compound 22 (31 mg, 0.027 mmol). The resulting mixture was stirred at ambient temperatures for 24 hours followed by removal of the solvent in vacuo. The resulting residue was purified via flash chromatography (NH$_3$ sat. MeOH/CHCl$_3$, 10:90), and the title compound 23 was isolated as a yellow amorphous solid (15 mg, 0.009 mmol, 33% yield). $^1$H NMR (400 MHz) d 2.03 (s, 12H), 2.08 (s, 24H), 2.25–2.39 (m, 16H), 3.22 (s, 6H), 3.38 (s, 8H), 3.68 (s, 12H), 4.10 (s, 4H), 6.54 (d, J=8.6 Hz, 4H), 6.97 (dd, J=2.3, 6.2 Hz, 4H), 7.03 (d, J=7.7 Hz, 2H), 7.09 (d, J=2.2 Hz, 6H), 7.23–7.27 (m, 2H), 7.32 (d, J=7.7 Hz, 2H), 7.51 (d, J=7.9 Hz, 2H), 7.89–7.97 (m, 12H), 8.05 (d, J=7.5 Hz, 2H), 8.11 (d, J=7.6 Hz, 2H); $^{13}$C NMR (90 MHz) d 37.8, 39.3, 42.4, 45.8, 55.0, 55.4, 55.7, 56.1, 57.3, 69.9, 84.8, 109.9, 123.4, 124.7, 124.9, 125.7, 126.5, 126.9, 127.5, 127.6, 128.1, 128.5, 129.3, 129.5, 130.3, 130.8, 131.3, 131.4, 135.3, 143.7, 147.7, 157.0, 171.0; IR (neat) 2940, 2766, 1661, 1598, 1496, 1462, 1365, 1250, 1112, 1031, 846, 711 cm$^{-1}$; HRMS calculated for $C_{96}H_{117}N_{10}O_6$ (M+H$^+$): 1505.9158 found: 1505.9106.

Example 6

Synthesis and Fluorescence Titrations of Various Chemosensors with AgClO$_4$

FIGS. 17–25 show fluorescence data for a selected number of sensors prepared in accordance with all or part of the method described above. The chemosensor of FIG. 19 was compound 23 prepared as described in Example 5.

Figure 17:
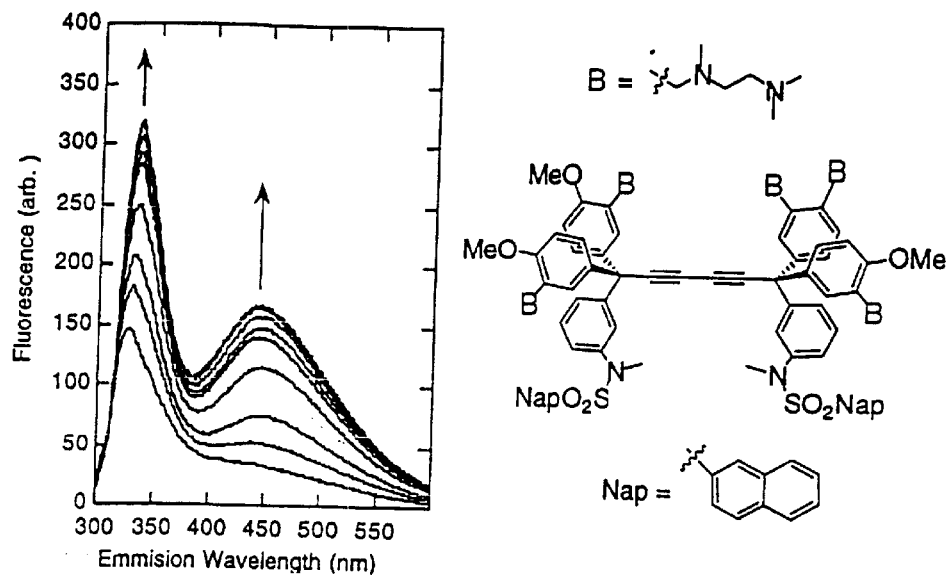
FIGS. 17–25 are graphs that show the effect of $AgClO_4$ on the fluorescence intensity of the indicated compounds.
Figure 18:
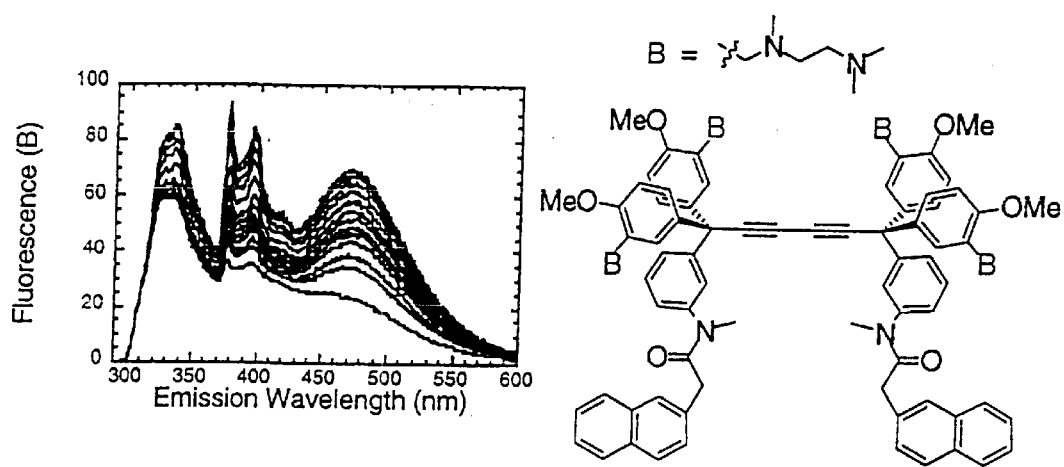

The chemosensor of FIG. 17 was prepared as described below. 1,1-dichloromethylmethyl ether (26 ml, 0.285 mmol) was added to a stirred solution of $CH_2Cl_2$ (2 ml) and compound 18 at 0° C. $TiCl_4$ (47 μl, 0.428 mmol) was added in a dropwise fashion to the reaction. The reaction was allowed to warm to ambient temperature over a period of 30 minutes. The mixture was slowly poured over ice, and the aqueous layer was extracted with $CH_2Cl_2$ (3×2 ml). The organic layer was dried over $MgSO_4$, and the solvent removed in vacuo. The resulting residue was purified via flash chromatography (EtOAc/Hex, 70:30) and the resulting tetraaldehyde was isolated as a yellow amorphous solid (52 mg, 0.043 mmol, 61%). $^1H$ NMR δ 3.16 (s, 6H), 3.88 (s, 12H), 6.82 (d, J=8.9 Hz, 4H), 6.96–7.00 (m, 4H), 7.16–7.26 (m, 4H), 7.39 (dd, J=2.6, 8.8 Hz, 4H), 7.43 (dd, J=1.8, 8.6 Hz, 2H), 7.54–7.62 (m, 8H), 7.81 –7.84 (m, 4H), 7.91 (d, J=8.0 Hz, 2H), 8.16 (s, 2H), 10.38 (s, 4H). $^{13}C$ NMR δ 38.5, 55.1, 56.2, 112.3, 123.6, 124.6, 125.5, 127.6, 127.8, 128.2, 128.3, 128.8, 129.2, 129.4, 129.5, 129.7, 132.4, 133.7, 135.2, 136.2, 136.7, 141.9, 144.8, 161.4, 189.7. IR (neat) 3010, 2943, 2863, 1682, 1603, 1492, 1349, 1282, 1256, 1163, 1072, 911, 816, 650 $cm^{-1}$. HRMS for $M+Na^+$ calculated for $C_{72}H_{56}N_2O_{12}S_2Na$: 1227.1372, found: 1227.3120.

AcOH (1.5 ml, glacial) was added to a stirred solution of EtOH (13.5 ml), the tetraaldehyde (241 mg, 0.20 mmol), and N,N,N'-trimethyl ethylenediamine (0.76 ml, 6.0 mmol). THF was added dropwise to the solution until all reactants had dissolved. The reaction was stirred at ambient temperature for 10 hours. $NaBH_3CN$ (251 mg, 4.0 mmol) was added to the solution, and the reaction was allowed to stir at ambient temperatures for 14 hours. The reaction mixture was added to 10% HCl (25 ml) and allowed to stir for 15 minutes. The reaction was then made basic (pH~10) with 10M NaOH. The aqueous layer was extracted with $CH_2Cl_2$. The organic layer was dried over $MgSO_4$, and removed in vacuo. The resulting residue was purified via flash chromatography ($NH_3$ sat. $MeOH/CHCl_3$, 10:90), and the title compound was isolated as a yellow amorphous solid (149 mg, 0.096 mmol, 48%). $^1H$ NMR δ 2.07–2.13 (m, 36H), 2.33–2.44 (m, 16H), 3.06 (s, 6H), 3.42 (s, 8H), 3.75 (s, 12H), 6.54 (d, J=8.7 Hz, 4H), 6.74 (ft, J=1.6 Hz, 2H), 6.86 (dd, J=2.5, 8.6 Hz, 4H), 7.06 (d, J=2.4 Hz, 4H), 7.08–7.11 (m, 2H), 7.21–7.30 (m, 4H), 7.39 (dd, J=1.6, 8.6 Hz, 2H), 7.52–7.61 (m, 4H), 7.73–7.79 (m, 4H), 7.86 (d, J=8.0 Hz, 2H), 8.15 (s, 2H). $^{13}C$ NMR δ 38.3, 42.6, 55.0, 55.6, 55.9, 56.4, 57.5, 70.0, 84.6, 109.9, 123.5, 125.9, 126.4, 126.9, 127.5, 128.1, 128.5, 128.7, 128.9, 129.1, 129.3, 129.5, 131.9, 132.2, 133.9, 135.0, 135.7, 141.4, 146.5, 157.1. IR (neat) 3054, 2942, 2817, 2414, 1601, 1496, 1463, 1349, 1251, 1162, 1131, 1031, 810, 737, 652 $cm^{-1}$. HMS for $M+H^+$ calculated for $C_{92}H_{113}N_{10}O_8S_2$: 1549.8184, found: 1549.8210.

The chemosensors of FIGS. 18 and 20–25 were prepared from compound 22 (See Example 5 and FIG. 16) as follows. The chemosensor of FIG. 18—A solution of methylene chloride (1.8 ml), triethylamine (0.2 ml), compound 22 (34 mg, 29 μmol), and 2-naphthylacetyl chloride (30 mg, 145 μmol) was stirred at ambient temperature for 2 hours. The reaction was quenched with sat. $NaHCO_3$, and then made very basic (pH>10) with 10 M NaOH. The aqueous layer was extracted with methylene chloride (3×5 ml). The solvent was removed in vacuo, and the resulting residue was purified using flash chromatography ($NH_3$ sat. $MeOH/CHCl_3$, 10:90). The title compound was isolated as a white amorphous solid (23 mg, 15.3 μmol, 53% yield).

Figures 19, 20:
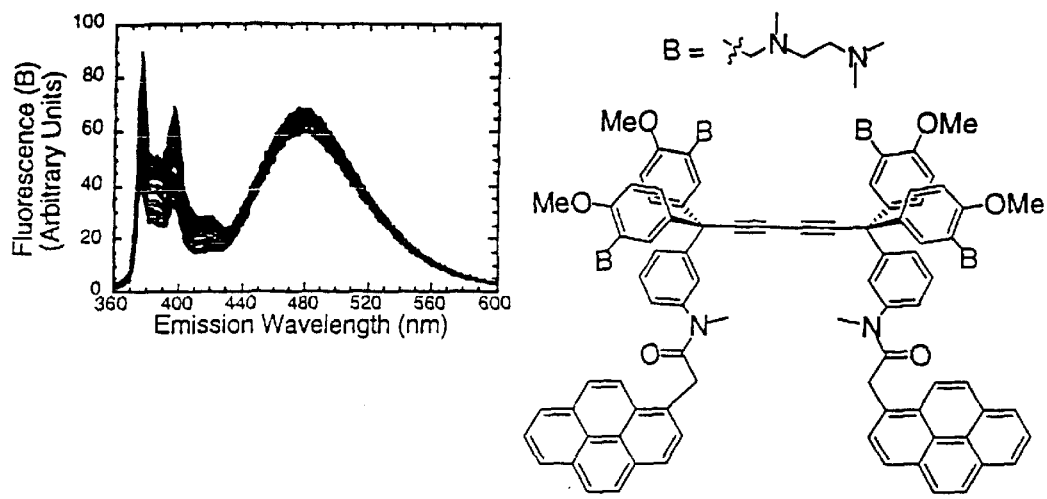

The chemosensor of FIG. 20—A solution of pyridine (2 ml), dimethylaminopyridine (1 mg, 6 μmol), compound 22 (26 mg, 22 μmol), and 2,6-dansyl chloride (36 mg, 132 μmol) was stirred at 70° C. for 17 hours. The solvent was removed in vacuo, and the resulting residue was purified using flash chromatography ($NH_3$ sat. $MeOH/CHCl_3$, 10:90). The title compound was isolated as a yellow amorphous solid (17.4 mg, 10.6 μmol, 48% yield).

Figure 21:
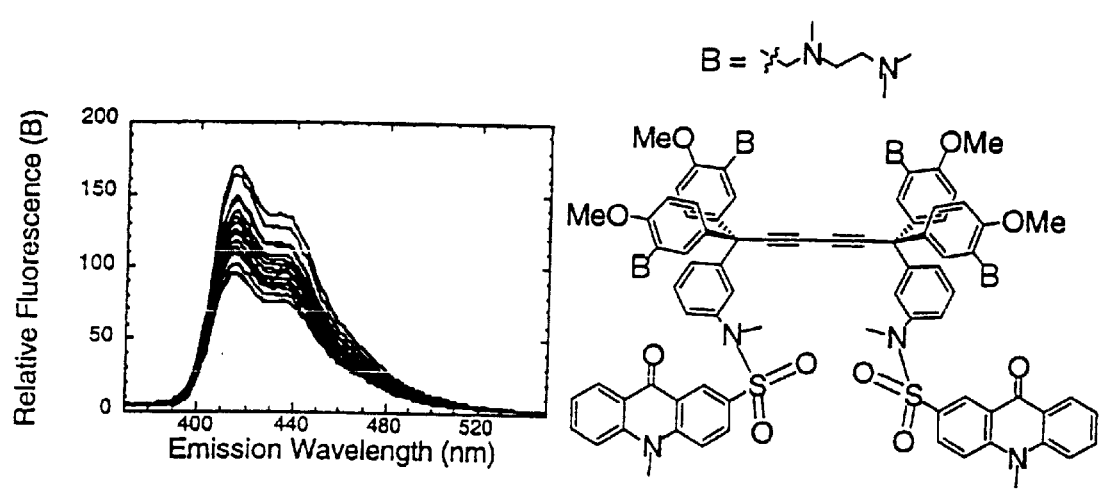

The chemosensor of FIG. 21—A solution of methylene chloride (1.8 ml), triethylamine (0.2 ml), compound 22 (38 mg, 33 μmol), and acridonesulfonyl chloride (41 mg, 132 μmol) was stirred at ambient temperature for 17 hours. The solvent was removed in vacuo, and the resulting residue was purified using flash chromatography ($NH_3$ sat. $MeOH/CHCl_3$, 10:90). The title compound was isolated as a yellow amorphous solid (7.2 mg, 4.2 μmol, 13% yield).

Figure 22:
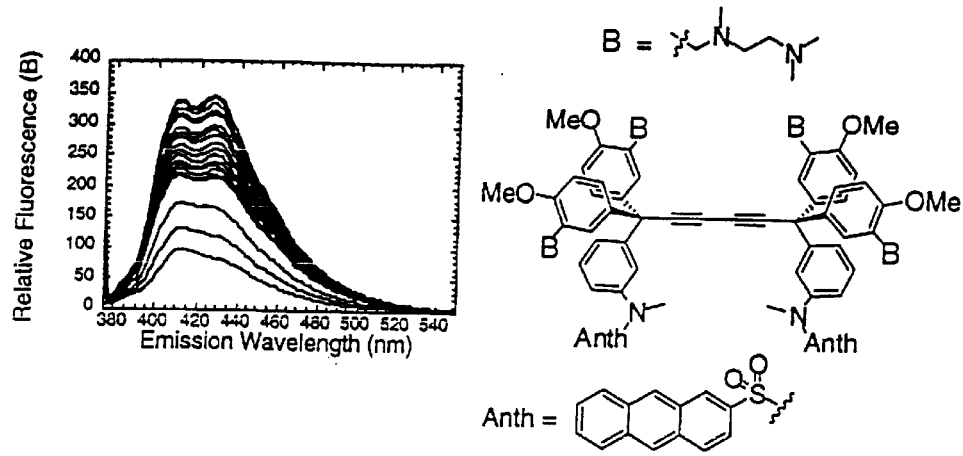

The chemosensor of FIG. 22—A solution of pyridine (1 ml), dimethylaminopyridine (0.4 mg, 3 μmol), compound 22 (15 mg, 13 μmol), and 2-anthracenesulfonyl chloride (14 mg, 52 μmol) was stirred at ambient temperature for 48 hours. The solvent was removed in vacuo, and the resulting residue was purified using flash chromatography ($NH_3$ sat. $MeOH/CHCl_3$, 10:90). The title compound was isolated as a yellow amorphous solid (10.9 mg, 6.6 μmol, 52% yield).

Figure 23:
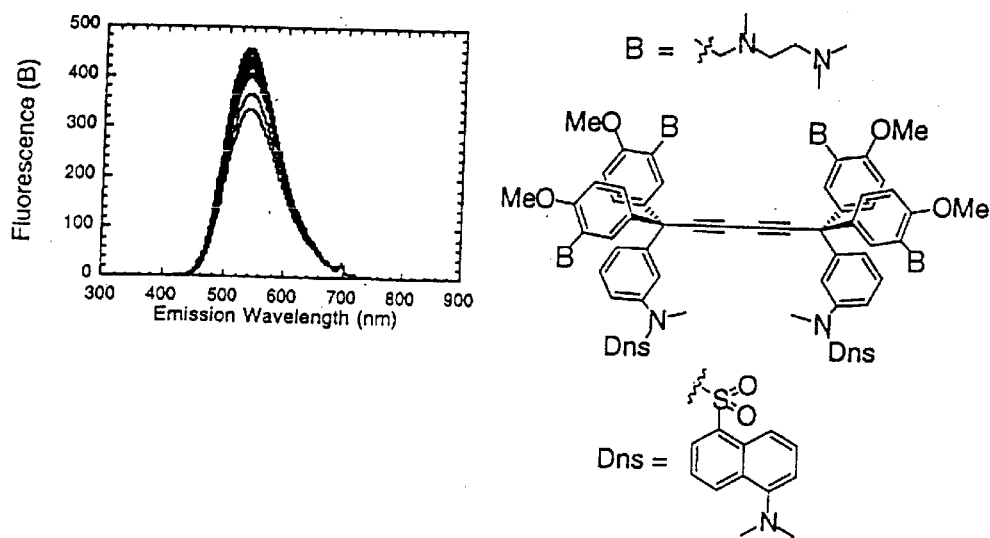

The chemosensor of FIG. 23—A solution of pyridine (2 ml), dimethylaminopyridine (1 mg, 6 μmol), compound 22 (35 mg, 30 μmol), and dansyl chloride (49 mg, 180 μmol) was stirred at 90° C. for 2 hours. The solvent was removed in vacuo, and the resulting residue was purified using flash chromatography ($NH_3$ sat. $MeOH/CHCl_3$, 10:90). The title compound was isolated as a yellow amorphous solid (22 mg, 13.4 μmol, 45% yield).

Figure 24:
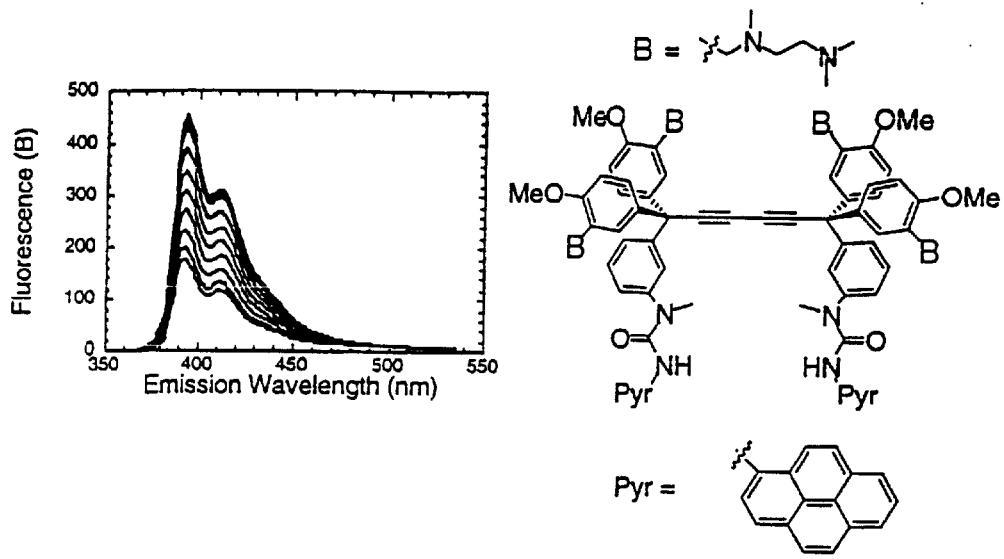

The chemosensor of FIG. 24—A solution of toluene (2 ml) and 1-pyrenyl azide (10 mg, 36 μmol) was stirred at reflux for 2.5 hours. Compound 22 (20 mg, 17 μmol) was added, and the reaction was stirred at reflux for 2 hours. The solvent was removed in vacuo, and the resulting residue was purified using flash chromatography ($NH_3$ sat. $MeOH/CHCl_3$, 10:90). The title compound was isolated as a white amorphous solid (20 mg, 12.1 μmol, 71% yield).

Figure 25:
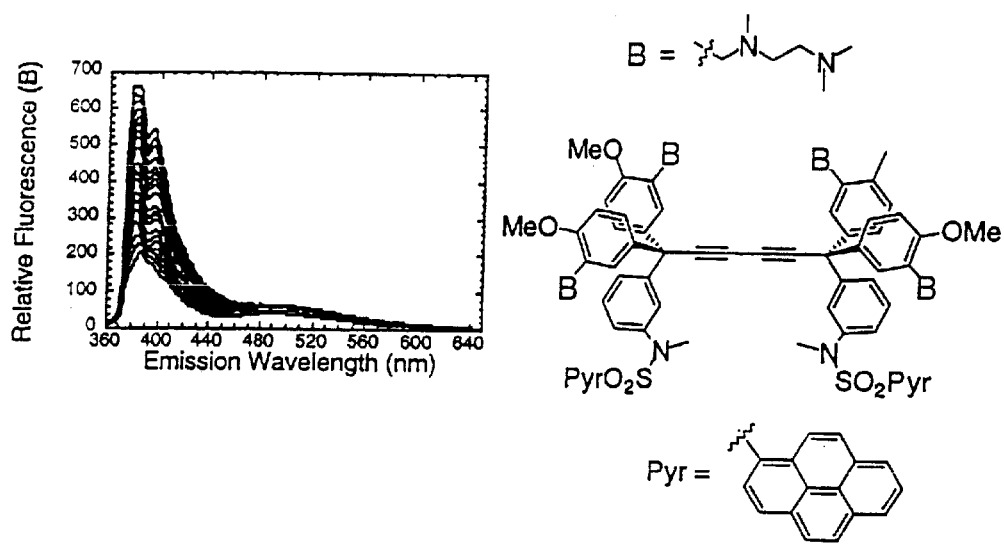

The chemosensor of FIG. 25—A solution of pyridine (1 ml), dimethylaminopyridine (0.4 mg, 3 μmol), compound 22 (15 mg, 13 μmol), and 1-pyrenesulfonyl chloride (16 mg, 52 μmol) was stirred at ambient temperature for 48 hours. The solvent was removed in vacuo, and the resulting residue was purified using flash chromatography ($NH_3$ sat. $MeOH/CHCl_3$, 10:90). The title compound was isolated as a yellow amorphous solid (11.6 mg, 6.8 μmol, 53% yield). Each of the foregoing chemosensors were analyzed as follows: samples of each chemosensor were prepared as solutions in MeCN (e.g., 2.5 ml, $1×10^{-6}$ M in MeCN), and then placed in a quartz fluorimeter cell (4 sided). A series of 2.5 μl aliquots of $AgClO_4$ ($1×10^{-3}$ M in MeCN) were then sequentially added to each sample. The fluorescence spectrum of each sample was recorded after each aliquot of $AgClO_4$ was added using a Shimadzu RF-5301PC spectrofluorimeter (excitation wavelength of 290 nm, excitation slit width=20 nm, emission slit width=5 nm; emission scanned from 300 nm to 600 nm).

The sensors tested all utilized trimethyl ethylenediamine binding groups and therefore responded to metal ions. The fluorescent groups differ among the various sensors. The fluorescent data presented is that which was seen upon titration of the sensor with $AgClO_4$ in acetonitrile solvent. Of note, the first three sensors (i.e., those shown in FIGS. 17–19) showed a ratiometric response to the analyte (AgClO$_4$). Ratiometric means that two peaks in the spectra vary independently such that the ratio of the two peaks can be used to indicate the concentration of analyte.

Other Embodiments

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

What is claimed is:

1. A compound having a structure selected from the group consisting of:

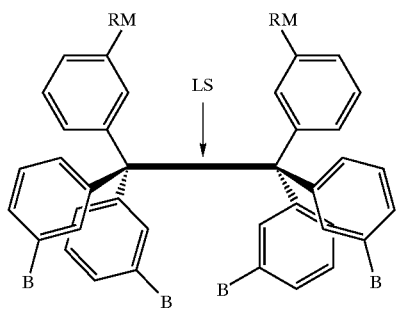

and

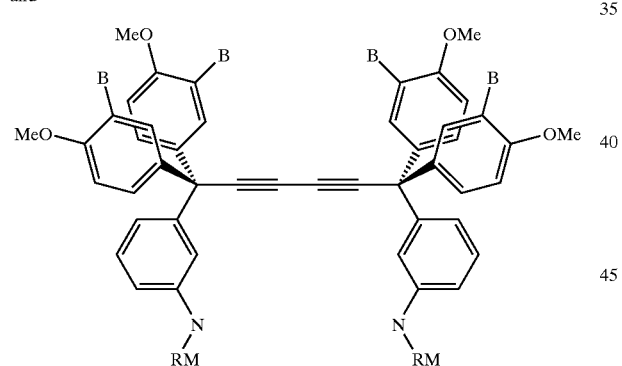

wherein B is an analyte-binding moiety, RM is a reporter moiety, and LS is a linear spacer.

2. The compound of claim 1, wherein B is a chemical group selected from ethylene diamine, trimethyl ethylenediamine, guanidinium,

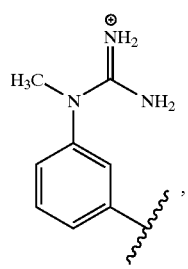 , 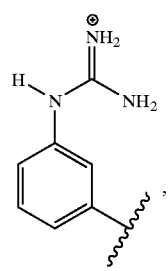 ,

-continued

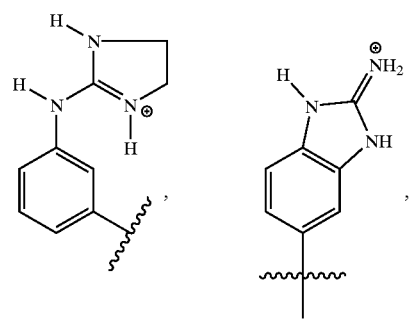 ,

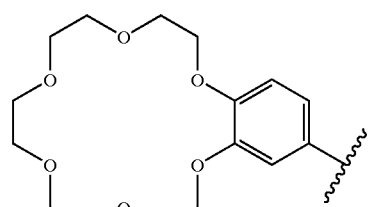 ,

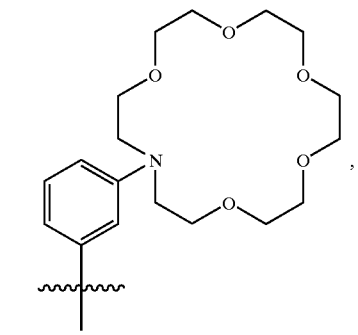 ,

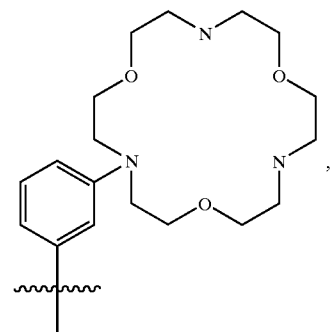 ,

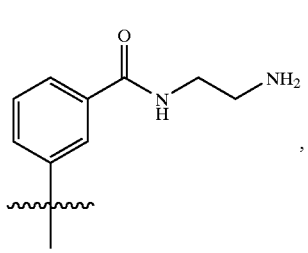 , 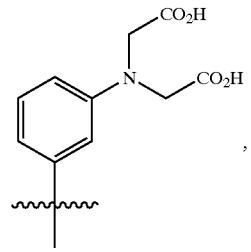 ,

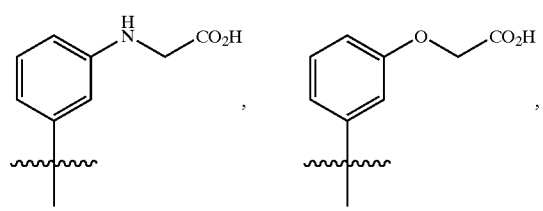
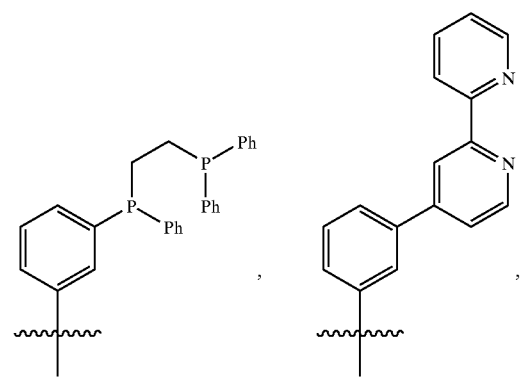
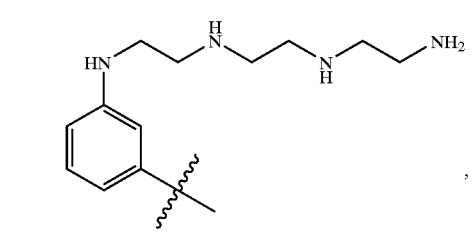
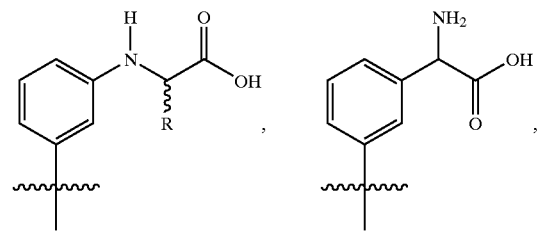
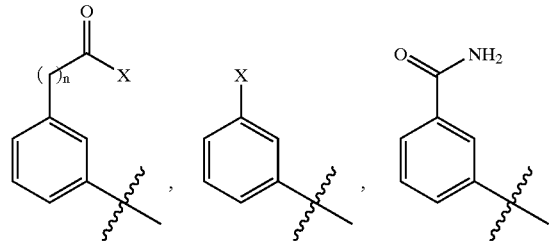
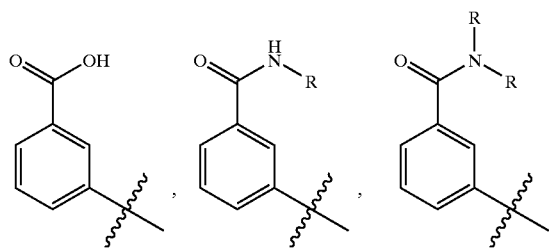
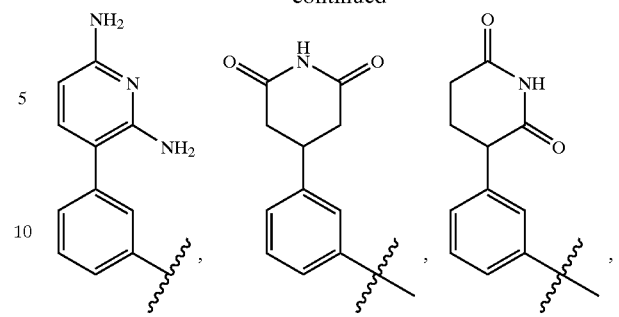
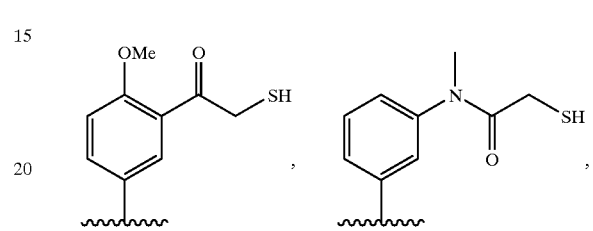
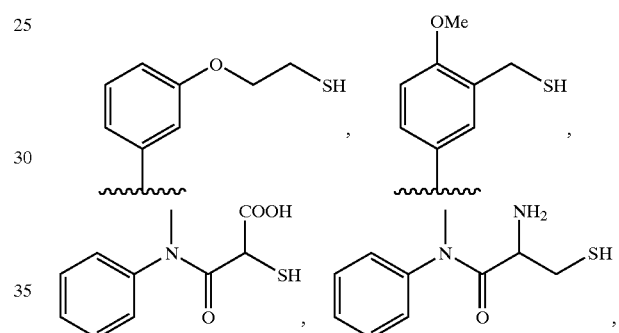
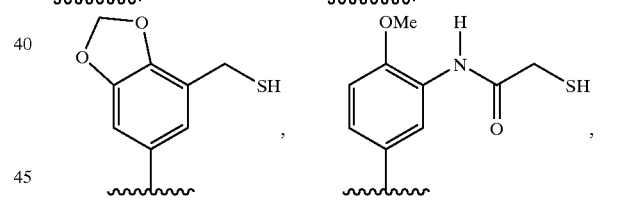
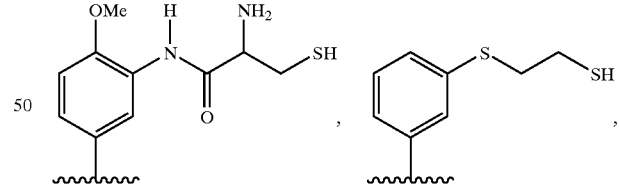
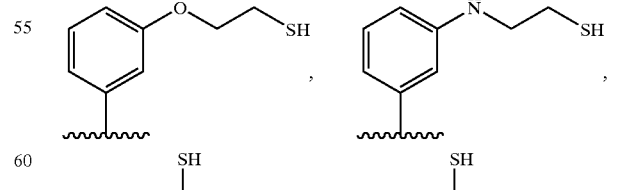
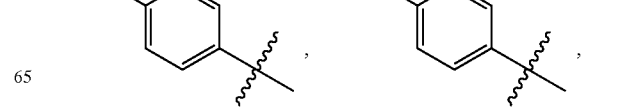

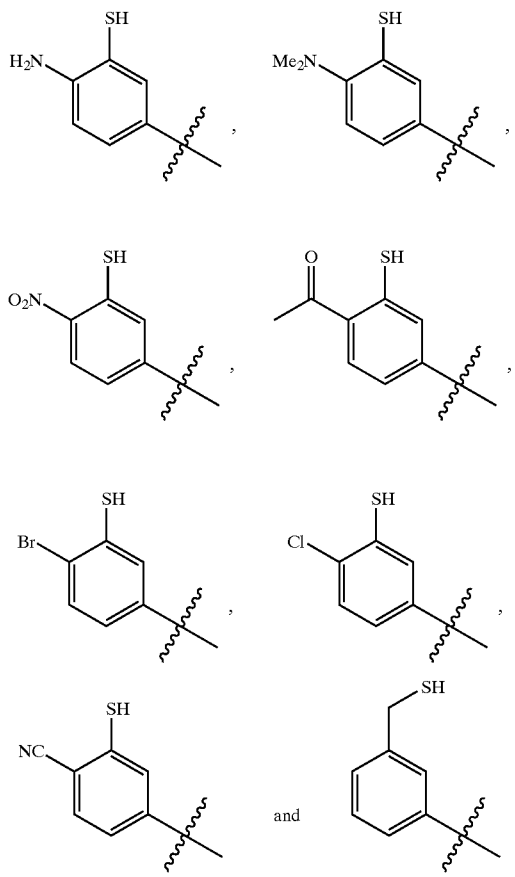
wherein X is selected from the group consisting —OH and —NH₂; and R is a chemical group that can be covalently attached to a nitrogen.
3. The compound of claim 1 where RM is a chemical group selected from napthyl, pyrenyl acetyl,
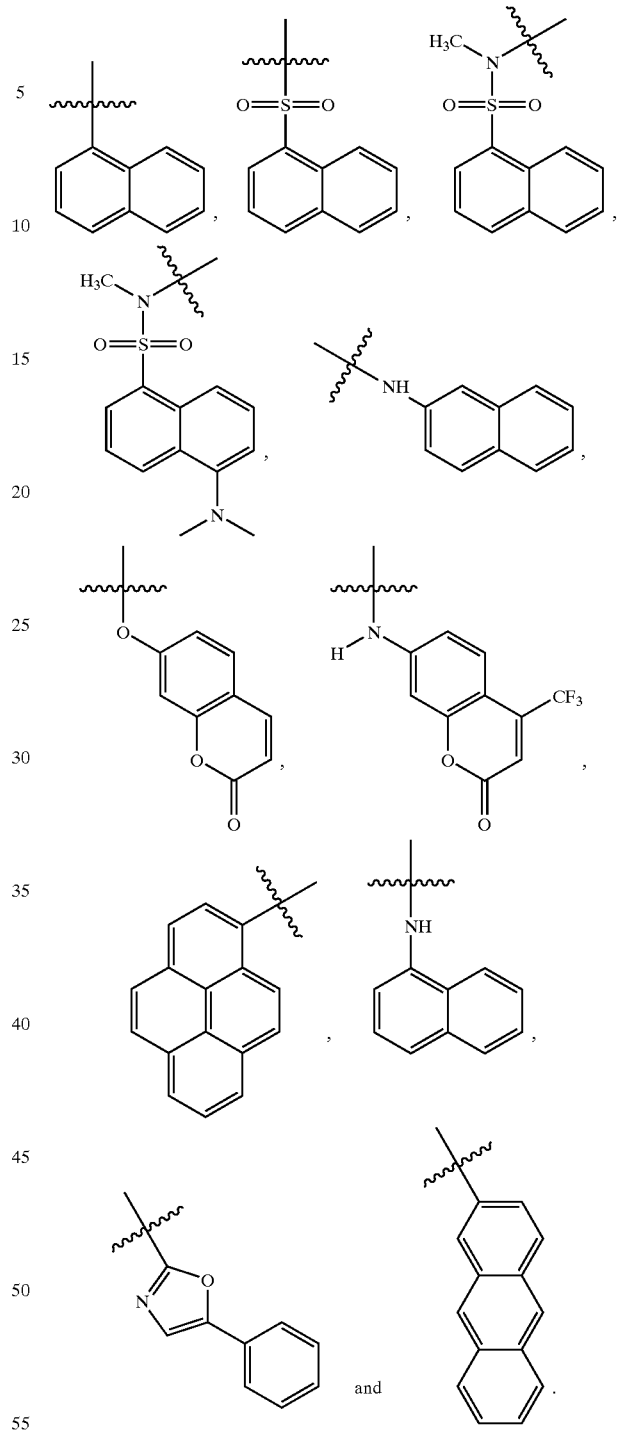
4. The compound of claim 2 where RM is a chemical group selected from napthyl, pyrenyl acetyl,
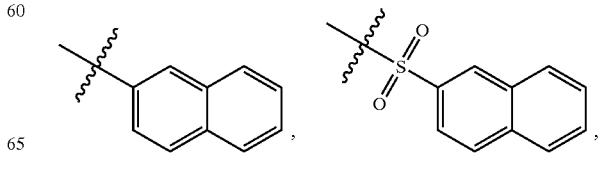

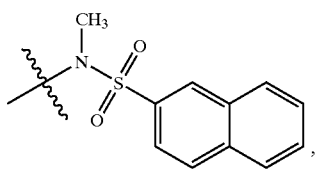

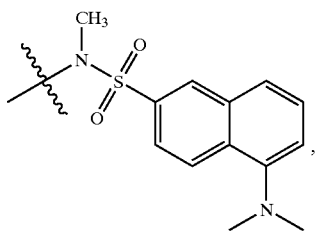

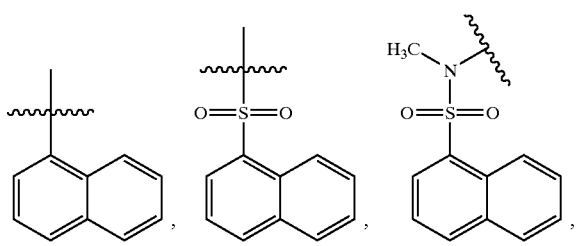

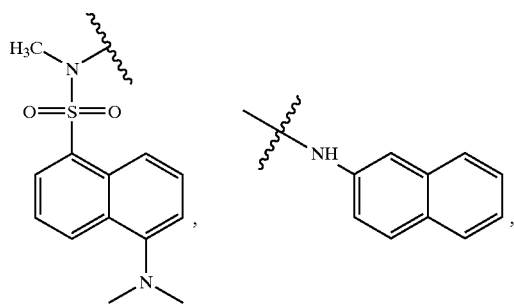

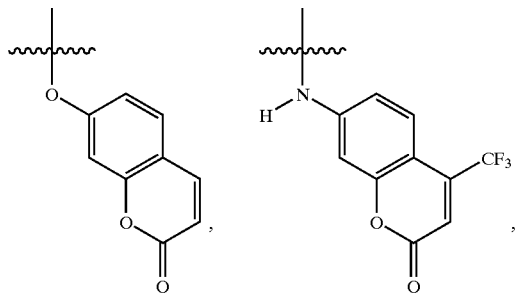

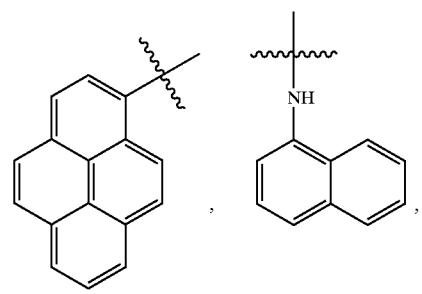

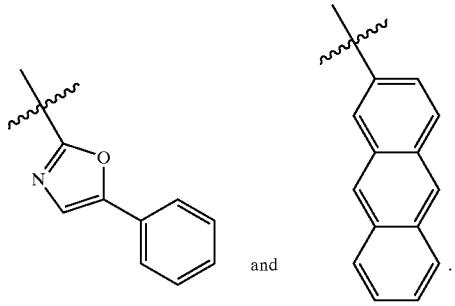

and.

5. The compound of claim 4, wherein B is ethylene diamine and RM is napthyl.

6. The compound of claim 4, wherein B is guanidinium and RM is napthyl.

7. The compound of claim 4, wherein B is trimethyl ethylenediamine and RM is pyrenyl acetyl.

8. The compound of claim 1, wherein LS is ethyne or butadiyne.

9. A method for preparing the compound of claim 1, comprising using in the synthesis of compound 1 a molecule selected from the group consisting of

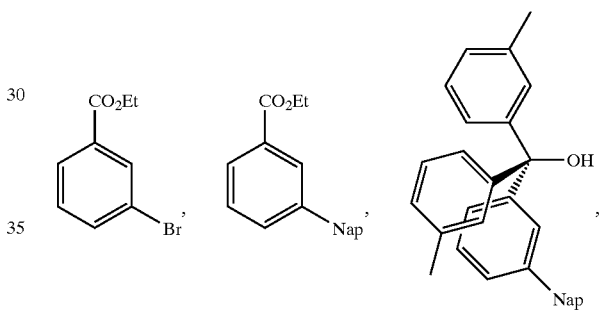

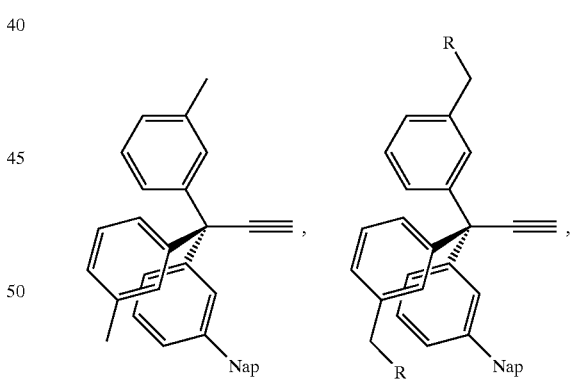

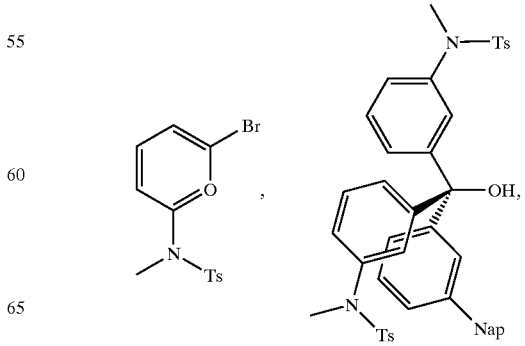

-continued
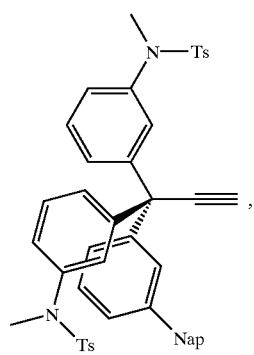
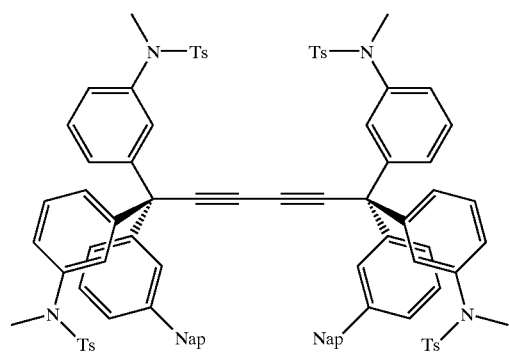
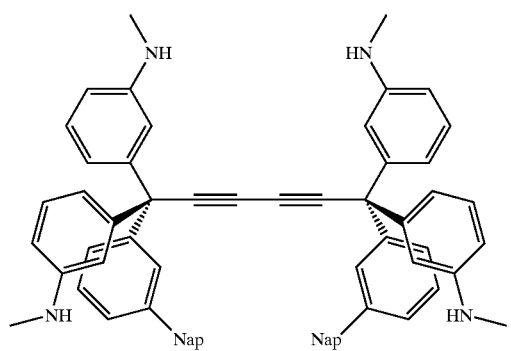
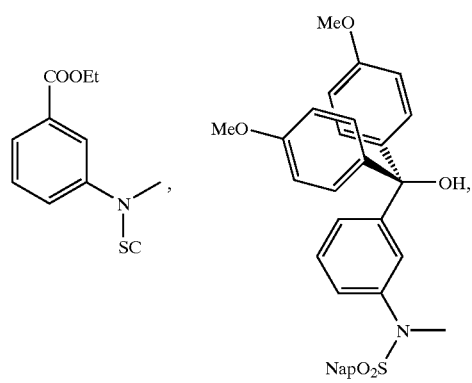
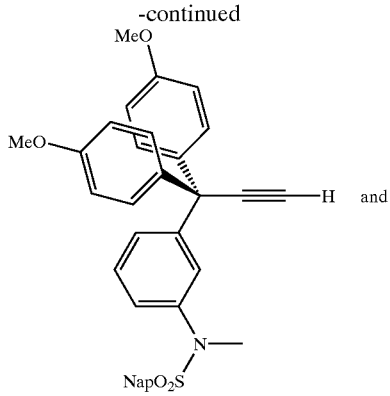
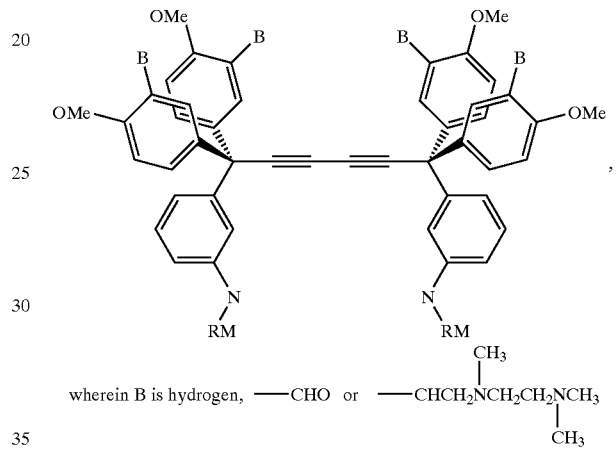
wherein B is hydrogen, —CHO or —CHCH$_2$NCH$_2$CH$_2$NCH$_3$ with CH$_3$ groups
and wherein RM is hydrogen, —SO$_2$Nap, or —COCF$_8$.
10. A compound according to claim 1 having the following structure:
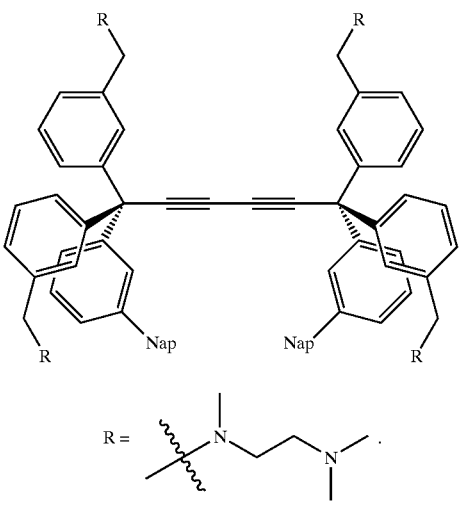
11. A compound according to claim 1 having the following structure:

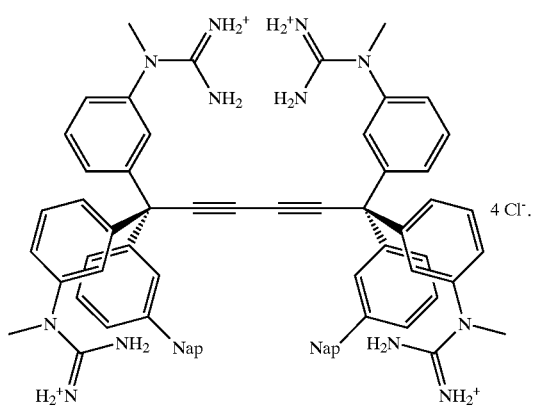

12. A compound according to claim 1 having the following structure:

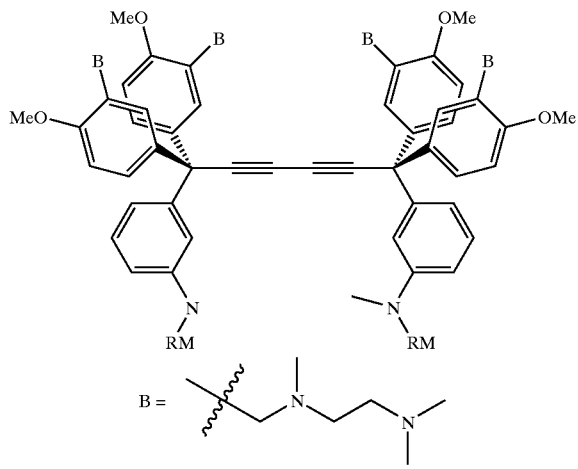

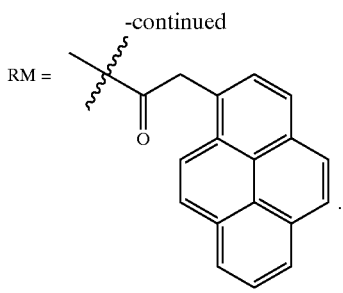

13. A method of preparing the compound of claim 1 comprising the step of covalently attaching an analyte-binding moiety and a reporter moiety to a molecule having a framework selected from the group consisting of bistrityl acetylene and bistrityl butadiyne.

14. A method of detecting an analyte using the compound of claim 1 comprising the steps of:
 providing a solution containing the analyte;
 adding one of the compounds of claim 1 to the solution; and
 measuring a signal from one of the compounds of claim 1 in the solution.

15. The method of claim 14, further comprising the step of quantifying the signal.

16. The method of claim 14, further comprising the step of placing the solution in a fluorescence analyzer.

17. The method of claim 14, wherein the step of measuring the signal is performed by measuring fluorescence emission from the solution.

18. A kit for determining the concentration of an analyte using one of the compound of claim 1 comprising:
 one of the compounds of claim 1 and
 instructions for using one of the compounds of claim 1 to determine the concentration of said analyte.

* * * * *